United States Patent
Blazar et al.

(10) Patent No.: US 11,390,848 B2
(45) Date of Patent: Jul. 19, 2022

(54) MATERIALS AND METHODS FOR MODIFYING THE ACTIVITY OF T CELLS

(71) Applicant: REGENTS OF THE UNIVERSITY OF MINNESOTA, Minneapolis, MN (US)

(72) Inventors: Bruce R. Blazar, Golden Valley, MN (US); Keli Hippen, Minneapolis, MN (US); Pavan Reddy, Ann Arbor, MI (US); Yaping Sun, Ann Arbor, MI (US); Ramiro Garzon, Columbus, OH (US)

(73) Assignees: Regents of the University of Minnesota, Minneapolis, MN (US); Regents of the University of Michigan, Ann Arbor, MI (US); The Ohio State University, Columbus, OH (US)

( * ) Notice: Subject to any disclaimer, the term of this patent is extended or adjusted under 35 U.S.C. 154(b) by 578 days.

(21) Appl. No.: 16/314,141

(22) PCT Filed: Jun. 28, 2017

(86) PCT No.: PCT/US2017/039739
§ 371 (c)(1),
(2) Date: Dec. 28, 2018

(87) PCT Pub. No.: WO2018/005640
PCT Pub. Date: Jan. 4, 2018

(65) Prior Publication Data
US 2019/0203173 A1 Jul. 4, 2019

Related U.S. Application Data

(60) Provisional application No. 62/355,654, filed on Jun. 28, 2016.

(51) Int. Cl.
C12N 5/0783 (2010.01)
C12N 15/113 (2010.01)
A61K 35/17 (2015.01)
A61P 37/06 (2006.01)

(52) U.S. Cl.
CPC ............ *C12N 5/0636* (2013.01); *A61K 35/17* (2013.01); *C12N 5/0637* (2013.01); *C12N 15/113* (2013.01); *A61P 37/06* (2018.01); *C12N 2310/113* (2013.01); *C12N 2320/32* (2013.01); *C12N 2501/65* (2013.01)

(58) Field of Classification Search
None
See application file for complete search history.

(56) References Cited

U.S. PATENT DOCUMENTS

2007/0232553 A1    10/2007  Baltimore et al.
2012/0064122 A1     3/2012  Baltimore et al.

FOREIGN PATENT DOCUMENTS

| EP | 1996022 | 12/2008 |
| WO | WO 2007/109350 | 9/2007 |
| WO | WO 2012/037043 | 3/2012 |

OTHER PUBLICATIONS

Haftmann et al., 2015, J. Immunol. Methods vol. 426: 128-133.*
Krebs et al., 2013, JASN, vol. 24: 1955-1965.*
Yang et al., 2012, J. Exp. Med. vol. 209: 1655-1670.*
Jeker et al., 2013, Immunol. Rev. vol. 253: 65-81.*
Lin et al., 2014. J. CLin. INvest. vol. 124: 5352-5367.*
Saki et al., 2015, IJHOSCR vol. 9, pp. 33-49.*
Ahn et al. "MicroRNA-146b promotes adipogenesis by suppressing the SIRT1-FOXO1 cascade," EMBO Mol. Med., 5(10):1602-12, Oct. 2013.
Barbarulo et al., "Notch3 and canonical NF-κB signaling pathways cooperatively regulate Foxp3 transcription," J. Immunol., 186(11):6199-206, Jun. 2011.
Bhairavabhotla et al., "Transcriptome profiling of human FoxP3+ regulatory T cells," Hum. Immunol., 77(2):201-13, Feb. 2016.
Burger et al., "Premalignant PTEN-deficient thymocytes activate microRNAs miR-146a and miR-146b as a cellular defense against malignant transformation," Blood, 123(26):4089-100, Jun. 2014.
Chatzigeorgiou et al., "Blocking CD40-TRAF6 signaling is a therapeutic target in obesity-associated insulin resistance," Proc. Natl. Acad. Sci. USA., 111(7):2686-91, Feb. 2014.
De Candia et al., "Serum microRNAs as Biomarkers of Human Lymphocyte Activation in Health and Disease," Front Immunol., 5:43, Feb. 2014.
Echavarria et al., "Angiopoietin-1 inhibits toll-like receptor 4 signalling in cultured endothelial cells: role of miR-146b-5p," Cardiovasc. Res., 106(3):465-77, Jun. 2015.
Gomez-Rodriguez et al., "Itk-mediated integration of T cell receptor and cytokine signaling regulates the balance between Th17 and regulatory T cells," J. Exp. Med., 211(3):529-43, Mar. 2014.
Gückel et al., "Cell-intrinsic NF-κB activation is critical for the development of natural regulatory T cells in mice," PLoS One, 6(5):e20003, 2011.
Hippen et al., "Generation and large-scale expansion of human inducible regulatory T cells that suppress graft-versus-host disease," Am. J. Transplant., 11(6):1148-57, Jun. 2011.
Hippen et al., "Massive ex vivo expansion of human natural regulatory T cells (T(regs)) with minimal loss of in vivo functional activity," Sci. Transl. Med., 3(83):83ra41, May 2011.

(Continued)

*Primary Examiner* — Amy E Juedes
(74) *Attorney, Agent, or Firm* — Fish & Richardson P.C.

(57) ABSTRACT

This disclosure provides miRNA/mRNA pairs that can be used to increase the efficacy of T cells or to down-modulate T cell efficacy and restore equilibrium.

5 Claims, 25 Drawing Sheets
Specification includes a Sequence Listing.

(56) References Cited

OTHER PUBLICATIONS

Hippen et al., "Umbilical cord blood regulatory T-cell expansion and functional effects of tumor necrosis factor receptor family members OX40 and 4-1BB expressed on artificial antigen-presenting cells," Blood, 112(7):2847-57, Oct. 2008.

Huang et al., "miR-142-3p restricts cAMP production in CD4+CD25- T cells and CD4+CD25+ TREG cells by targeting AC9 mRNA," EMBO rep., 10(2):180-5, Feb. 2009.

Jiang et al., "Molecular dissection of the miR-17-92 cluster's critical dual roles in promoting Th1 responses and preventing inducible Treg differentiation," Blood, 118(20):5487-97, Nov. 2011.

Lima et al., "MiRNA-146b-5p upregulates migration and invasion of different Papillary Thyroid Carcinoma cells," BMC Center, 16(1):108, Dec. 2016.

Lu et al., "Function of miR-146a in controlling Treg cell-mediated regulation of Th1 responses," Cell, 142(6):914-29, Sep. 2010.

Lu et al., "miR-146b antagomir-treated human Tregs acquire increased GVHD inhibitory potency," Blood, 128(10):1424-35, Sep. 2016.

Muto et al., "TRAF6 is essential for maintenance of regulatory T cells that suppress Th2 type autoimmunity," PLoS One, 8(9):e74639, Sep. 2013.

Okoye et al., "Transcriptomics identified a critical role for Th2 cell-intrinsic miR-155 in mediating allergy and antihelminth immunity," Proc. Natl. Acad. Sci. USA., 111(30):E3081-90, Jul. 2014.

O'Shaughnessy et al., "Ex vivo inhibition of NF-kappaB signaling in alloreactive T-cells prevents graft-versus-host disease," Am. J. Transplant, 9(3):452-62, Mar. 2009.

Park et al., "MicroRNA-146a and microRNA-146b regulate human dendritic cell apoptosis and cytokine production by targeting TRAF6 and IRAK1 proteins," J Biol. Chem., 290(5):2831-41, Jan. 2015.

PCT International Preliminary Report on Patentability in International Appln. No. PCT/US2017/039739 dated Jan. 1, 2019, 11 pages.

PCT International Search Report and Written Opinion in International Appln. No. PCT/US2017/039739 dated Oct. 18, 2017, 22 pages.

Racker et al., "Glycolysis and methylaminoisobutyrate uptake in rat-1 cells transfected with ras or myc oncogenes," Proc. Natl. Acad. Sci. USA., 82(11):3535-8, Jun. 1985.

Ranganathan et al., "Regulation of acute graft-versus-host disease by microRNA-155," Blood, 119(20):4786-97, May 2012.

Singh et al., "MicroRNA-15b/16 Enhances the Induction of Regulatory T Cells by Regulating the Expression of Rictor and mTOR," J. Immunol., 195(12):5667-77, Dec. 2015.

Stahl et al., "miR-155 inhibition sensitizes CD4+ Th cells for TREG mediated suppression," PLoS One, 4(9):e7158, Sep. 2009.

Stickel et al., "MiR-146a regulates the TRAF6/TNF-axis in donor T cells during GVHD," Blood, 124(16):2586-95, 2014.

Sun et al., "Allogeneic T cell responses are regulated by a specific miRNA-mRNA network," J. Clin. Invest., 123(11):4739-54, Nov. 2013.

Testa et al., "miR-146 and miR-155: two key modulators of immune response and tumor development," Non-coding RNA, 3(3):22, Sep. 2017.

Wang et al., "The transcription factor Myc controls metabolic reprogramming upon T lymphocyte activation," Immunity, 35(6):871-82, Dec. 2011.

Warth et al., "Induced miR-99a expression represses Mtor cooperatively with miR-150 to promote regulatory T-cell differentiation," EMBO J., 34(9):1195-21, May 2015.

Wei et al., "Autophagy enforces functional integrity of regulatory T cells by coupling environmental cues and metabolic homeostasis," Nat. Immunol., 17(3):277-85, Mar. 2016.

Zhao et al., "Selective depletion of CD4+CD25+Foxp3+ regulatory T cells by low-dose cyclophosphamide is explained by reduced intracellular ATP levels," Cancer Res., 70(12):4850-8, May 2010.

\* cited by examiner

| | miRs Most Dysregulated | Genes Most Dysregulated |
|---|---|---|
| tTreg vs. Teff (miRNA up; mRNA up) | hsa-miR-423-5p<br>hsa-miR-29b-3p | IL1A<br>FOXP3 |
| R/T iTreg vs. Teff (miRNA up; mRNA up) | hsa-miR-30e-5p<br>hsa-miR-181a-2-3p<br>hsa-miR-125a-3p<br>hsa-miR-24-2-5p<br>hsa-miR-423-5p<br>hsa-miR-92b-5p<br>hsa-miR-324-3p | FOXP3<br>IL23A |
| tTreg vs. R/T iTreg (miRNA up; mRNA up) | None | None |

Figure 7B

MATERIALS AND METHODS FOR MODIFYING THE ACTIVITY OF T CELLS

CROSS-REFERENCE TO RELATED APPLICATIONS

This application is a National Stage application under 35 U.S.C. § 371 of International Application No. PCT/US2017/039739 having an International Filing Date of Jun. 28, 2017, which claims the benefit of U.S. Application No. 62/355,654 filed Jun. 28, 2016. The disclosure of the prior application is considered part of (and is incorporated by reference in) the disclosure of this application.

FEDERALLY SPONSORED RESEARCH OR DEVELOPMENT

The invention was made with government support under CA065493, HB037164, HL114512, HL118979, HL090775, CA173878 and HL128046 awarded by the National Institutes of Health. The government has certain rights in the invention.

TECHNICAL FIELD

This disclosure generally relates to T cells.

BACKGROUND

Adoptive cellular therapy using regulatory T (Treg) cells is an effective treatment in many animal models of diseases including autoimmunity, organ rejection, and graft-versus-host-disease (GVHD) following stem cell transplantation. Translating these findings into a human therapeutic, however, has been difficult, largely because of the high numbers of very pure cells that are required to reproducibly suppress disease. An additional hurdle is that Treg cells do not persist long term after adoptive transfer, although persistence does not necessarily correlate with efficacy. Therefore, optimizing the survival, stability and suppressive function of Treg cells are critical for maximizing the therapeutic potential of these cells.

SUMMARY miRNA/mRNA pairs are described herein that can be used to increase the efficacy of Treg cells or to down-modulate Treg efficacy and restore equilibrium. This disclosure demonstrates that knock-down of specific miRNAs increased tTreg survival and function in vitro. This disclosure also demonstrates the in vivo safety of tTreg treated with anti-miRs (antagomirs) using a xenogeneic model of GVHD (see, for example, Hippen et al. (2011, Sci. Transl. Med., 3(83):83ra41); Hippen et al. (2011, Am. J. Transplant., 11(6):1148-57); and Hippen et al. (2008, Blood, 112(7):2847-57)).

In one aspect, a method of increasing the survival, stability and/or function of T cells is provided. Such a method typically includes providing T cells from an individual; contacting the T cells with at least one moiety that decreases or inhibits miRNA-146b, miRNA-4484 or miRNA-155; and introducing the contacted T cells back into the individual. Representative moieties include, without limitation, nucleic acid molecules, small molecules, polypeptides, and anti-miRs. Representative nucleic acid molecules include RNA interference molecules. Representative polypeptides include antibodies. Representative anti-miRs are antagomirs.

In some embodiments, the T cells are contacted with the moiety on day 0. In some embodiments, the T cells are cultured for about 1 to about 21 days before being contacted with the moiety. In some embodiments, the T cells are contacted with the moiety for several hours to several days to several weeks.

In some embodiments, the T cells are Treg cells. In some embodiments, the Treg cells are tTreg cells or iTreg cells.

In another aspect, an article of manufacture is provided. Such an article of manufacture typically includes at least one moiety that decreases or inhibits miRNA-146b, miRNA-4484 or miRNA-155. In some embodiments, the at least one moiety is a nucleic acid molecule, a small molecule, a polypeptide, and an anti-miR.

In one aspect, methods of increasing the survival, stability and/or function of T cells are provided. Such methods typically include providing T cells from an individual; contacting the T cells with at least one moiety that decreases or inhibits one or more miRNAs; and introducing the contacted T cells back into the individual. Representative moieties include, without limitation, nucleic acid molecules (e.g., RNA interference), small molecules, polypeptides (e.g., antibodies), and anti-miRs (e.g., antagomirs). In some embodiments, the miRNAs is one of the miRNAs shown in Table 3.

In some embodiments, the T cells are contacted with the moiety on day 0. In some embodiments, the T cells are cultured for about 1 to about 21 days before being contacted with the moiety. In some embodiments, the T cells are contacted with the moiety for several hours to several days to several weeks. In some embodiments, the T cells are Treg cells. In some embodiments, the Treg cells are tTreg cells or iTreg cells.

In another aspect, methods of decreasing the activity of T cells are provided. Such methods typically include providing T cells from an individual; contacting the T cells with at least one moiety that increases or induces one or more miRNAs; and introducing the contacted T cells back into the individual. Representative moieties include, without limitation, nucleic acid molecules (e.g., RNA interference), small molecules, polypeptides (e.g., antibodies), and anti-miRs (e.g., antagomirs). In some embodiments, the miRNAs is one of the miRNAs shown in Table 3.

In some embodiments, the T cells are contacted with the moiety on day 0. In some embodiments, the T cells are cultured for about 1 to about 21 days before being contacted with the moiety. In some embodiments, the T cells are contacted with the moiety for several hours to several days to several weeks. In some embodiments, the T cells are Treg cells. In some embodiments, the Treg cells are tTreg cells or iTreg cells.

In another aspect, an article of manufacture is provided that includes at least one moiety that decreases or inhibits one or more miRNAs. Representative moieties include, without limitation, nucleic acid molecules (e.g., RNA interference), small molecules, polypeptides (e.g., antibodies), and anti-miRs (e.g., antagomirs). In some embodiments, the miRNAs is one of the miRNAs shown in Table 3.

In one aspect, an article of manufacture is provided that includes at least one moiety that increases or induces one or more miRNAs. Representative moieties include, without limitation, nucleic acid molecules (e.g., RNA interference), small molecules, polypeptides (e.g., antibodies), and antimiRs (e.g., antagomirs). In some embodiments, the miRNAs is one of the miRNAs shown in Table 3.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 7B provides the mRNA CLIPChIP profiles of tTreg, Rapa/TGFβ iTreg and Teff cells. The 'miRs Most Dysregulated' is a list of the miRNAs that were most differentially expressed between the indicated groups using the AGO/CLIP assay. The black or red coding identifies which targets were or were not identified on the traditional miRNA array, respectively. The 'Genes Most Dysregulated' is a list of genes that are known to control Treg survival, stability, and/or function, and are known or predicted targets of the associated miRNA species.

DETAILED DESCRIPTION

Figure 1A:
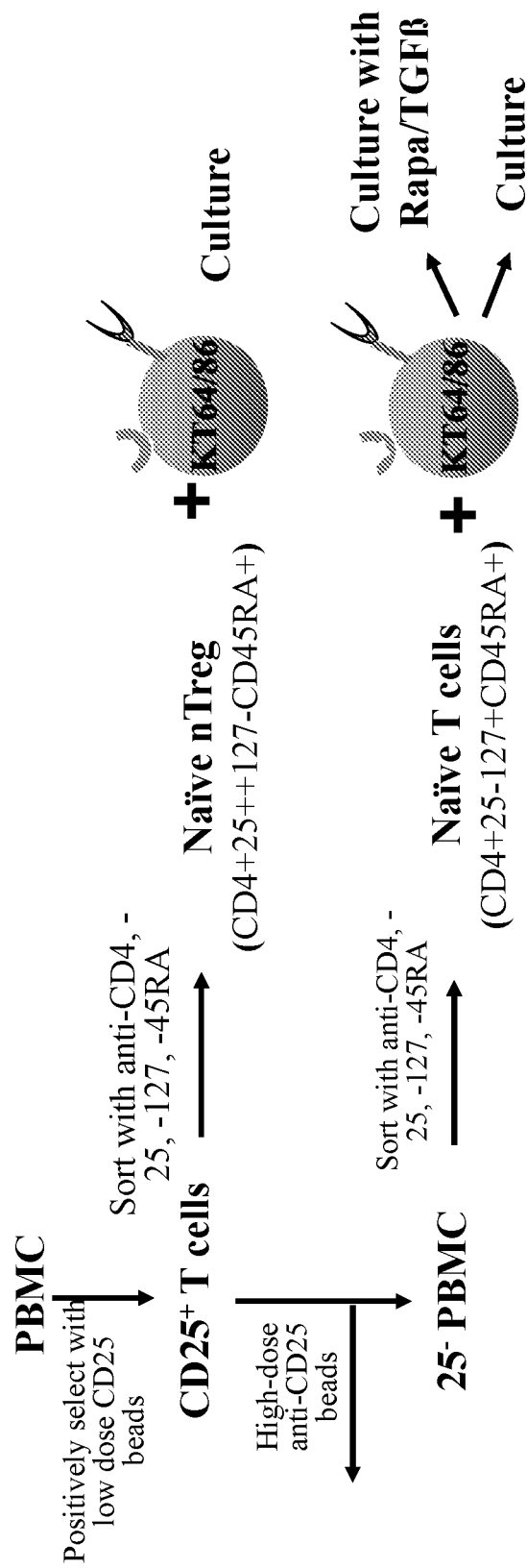
FIG. 1A is a schematic showing an outline of the cell sorting experiments that were applied to assess miRNA expression in tTreg, iTreg and Teff (n=3 donors).

Treg cells develop in the thymus (tTreg) or they can be induced in the periphery (pTreg) in response to environmental cues (e.g., chronic infection). Many of these environmental cues also can be used to induce suppressive function following stimulation in vitro, and these Tregs are denoted iTreg. Because of their relatedness, information on iTreg signaling and function is expected to be directly translatable to pTreg.

MicroRNAs (miRNAs or miRs) are short (~22 nucleotides), single-stranded RNA molecules that, among other functions, fine-tune the responses of T cells and Treg cells to self-, environmental-, and foreign-antigens. miRs regulate the expression of genes by hybridizing to target sites with complementary sequences, resulting in translational repression, mRNA cleavage, and/or destabilization through effector RNA-mediated silencing complexes (RISCs) or argonaute containing (AGO-containing) micro-ribonucleoprotein (miRNP) effector complexes. Because individual miRs target multiple mRNA species, and individual mRNAs are targeted by multiple miRs, traditional mRNA and miRNA microarray analyses cannot identify specific miRNA-mRNA partners.

A platform has been developed that can be used to determine specific miRNA species that are actively targeting mRNA, and which mRNA species are bound to miRNA. See, for example, Sun et al., 2013, J. Clinical Invest., 123:4793-54. This platform was used to identify miRNA-mRNA pairs that are differentially expressed in expanded tTreg or iTreg cells relative to control in vitro expanded CD4+ cells (herein referred to as Teff cells). Using these methods, novel miRNA-mRNA associations are described that control tTreg and iTreg survival, stability and/or function.

The miRNA/mRNA pairs described herein can be used to increase the efficacy (e.g., suppressive function) of Treg cells, e.g., to suppress autoimmunity, graft rejection or GVHD. Also, the miRNA/mRNA pairs described herein can be used to down-modulate Treg efficacy and restore equilibrium, since overly active regulatory T cells are associated with tumor persistence and chronic infections. In addition, the miRNA/mRNA pairs described herein can be used to increase the suppressive function of non-Treg cells, e.g., to suppress autoimmunity, graft rejection or GVHD. As used herein, non-Treg cells include, without limitation, naïve T cells, effector cells, effector memory cells, memory stem cells, central memory cells, short-lived effector cells, and long-lived effector cells.

Therefore, methods are provided herein that can be used to increase the survival, stability and/or function of T cells, or, alternatively, decrease the activity of T cells. Such methods typically include providing T cells from an individual (e.g., in vivo or ex vivo) and contacting the T cells with at least one moiety that decreases or inhibits one or more miRNAs or that increases or induces one or more miRNAs. In instances where the contacting step is performed ex vivo, the method further includes introducing the contacted T cells back into the individual. In instances where the contacting step is performed in vivo, the moiety that decreases or inhibits one or more miRNAs or that increases or induces one or more miRNAs can be delivered using, for example, antibody- or ligand-targeted nanoparticles, liposomes, viral or non-viral delivery systems, or other types of DNA- or RNA-based delivery systems.

Methods of obtaining T cells from an individual are known in the art, as are methods of returning the T cells back into an individual after the cells have been manipulated in the desired manner. Methods of contacting T cells in an individual in vivo also are known in the art. The contacting can be transient (e.g., with a moiety that is designed to transiently decrease or inhibit one or more miRNAs or increase or induce one or more miRNAs) or the contacting can be permanent (e.g., with a moiety that is designed to permanently decrease or inhibit one or more miRNAs or increase or induce one or more miRNAs). It would be understood that, in some instances, the difference between transient effects and permanent effects is genetic engineering (e.g., genetically engineering the T cells to express the moiety). As used herein, transient can refer to hours, days, or weeks, and transient also can refer to the contacting step and/or the effects of the contacting step (e.g., on the one or more miRNAs).

A well-known class of moieties that down-regulate miRNAs are anti-miRs, which includes a group of compounds known as antagomirs. However, other moieties that down-regulate or up-regulate the indicated miRNAs can be used and include, without limitation, nucleic acid molecules, polypeptides (e.g., antibodies), or small molecules. Nucleic acids include, for example, RNA interference nucleic acids (e.g., shRNA, siRNA, RNAi) or gene editing nucleic acids (e.g., CRISPRs, TALENs, zinc finger nucleases, megaTALs).

As described herein, the miRNAs that can be down-regulated to increase the survival, stability and/or function of T cells or up-regulated to decrease the activity of T cells are shown, without limitation, in Table 3.

Moieties as used herein refer to those moieties that act directly on the miRNAs identified herein and also those moieties that act indirectly but still effect the result on the miRNAs identified herein. For example, an increase or induction in one or more miRNAs can occur due to disruption or inhibition of negative regulators (e.g., a different miRNAs) or due to activation or increased expression of positive regulators, or by engaging an enhancer or super-enhancer region.

Any such moieties can be delivered to the T cells using methods and materials known in the art. Such methods and materials include, without limitation, transduction of viral (e.g., lentiviral, retroviral) or non-viral vectors, lipofection, nanoencapsulation or nanoparticles (e.g., liposomes), electroporation, or delivery of naked RNA molecules.

As described herein, the T cells can be contacted with the moiety upon collection (e.g., at day 0) or anytime thereafter (e.g., day 1 to day 21). Since many miRNAs are induced following stimulation of the T cell receptors, early disruption (e.g., decrease or increase; inhibition or induction) can be beneficial. The conditions under which the T cells are cultured during the contacting step are known in the art. Depending upon the moiety, the contacting can take place for several hours, several days, or several weeks. Depending upon the moiety, the contacting may be repeated more than once (e.g., a plurality of contacting steps).

To determine whether the T cells have been sufficiently contacted with the moiety (e.g., contacted with an effective amount of the moiety for a time sufficient to decrease or inhibit one or more of the miRNAs identified herein or to increase or induce one or more of the miRNAs identified herein), the miR or the mRNA can be amplified using, for example, qRT-PCR. Alternatively, one or more protein products of the miR/mRNA interaction can be monitored using, for example, immunoassays (e.g., ELISA, Western blot)).

Alternatively, T cells can be evaluated (e.g., in vitro or in vivo) for cell suppression potency and/or survival using known methods.

Articles of manufacture also are provided herein that include at least one moiety that decreases or inhibits one or more of the miRNAs identified herein or that increases or induces one or more of the miRNAs identified herein, depending on the desired function (e.g., increasing the survival, stability and/or function of T cells or decreasing the activity of T cells). Articles of manufacture are known in the art and typically include one or more containers and packaging materials.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Cell Purification and Culture

Non-mobilized peripheral blood (PB) leukapheresis products were purchased from Memorial Blood Center (St. Paul, Minn.). Naïve human PB tTreg (CD4+25+127-45RA+) were sort-purified from PB mononuclear cells (PBMNCs) (Ficoll-Hypaque, Amersham Biosciences) in a two-step procedure in which CD25+ cells were initially enriched from PBMNCs by AutoMACS (PosselD2) with GMP grade anti-CD25 microbeads (Miltenyi Biotec). CD25+(high) cells were stained with CD4, CD8, CD25, CD127 and CD45RA and sorted via FACSAria as CD4+, CD8-, CD25+(high), CD127- and CD45RA+. Note that the bead-bound and fluorochrome-conjugated anti-CD25 antibodies recognize different epitopes (Miltenyi Biotec), followed by sorting on a FACSAria (BD Biosciences). Naïve human CD4 T cells were sort-purified from the CD25- fraction as CD4+, CD25-, CD127+, and CD45RA+.

Purified naïve tTreg and CD4 T cells were stimulated with a K562 cell line engineered to express CD86 and the high-affinity Fc receptor (CD64) (2:1 tTreg/KT), which had been irradiated with 10,000 cGy and incubated with anti-CD3 (Miltenyi Biotec). In some experiments, tTregs were stimulated with KT64/86 cells that were preloaded, irradiated, and frozen (1:1 tTreg/KT). Naive tTreg and CD4+ T cells were cultured in X-Vivo-15 (BioWhittaker, Walkersville, Md.) media supplemented with 10% human AB serum (Valley Biomedical). Recombinant IL-2 (300 IU/mL for Treg, 50 IU/mL for control T cells; Chiron, Emeryville, Calif.) was added on day 2 and maintained for culture duration. Cultures were maintained at $0.25 \times 10^6$ to $0.5 \times 10^6$ viable nucleated cells/ml every 2 to 3 days. Rapa/TGFbeta iTreg and Teff cultures were re-stimulated on day 7, and tTreg were re-stimulated on day 12 with fresh KT64/86 (2:1 tTreg/KT), and were kept in culture until days 14 and 19, respectively.

Figure 1B:
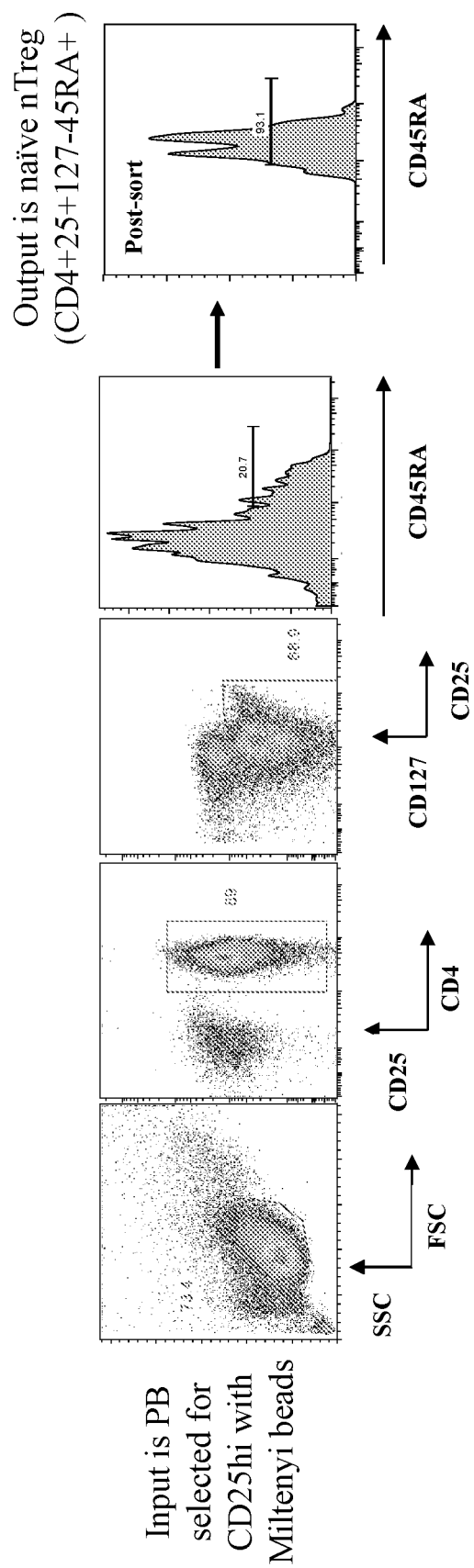
FIG. 1B is a representative FACS histogram showing purified tTregs.
Figure 2:
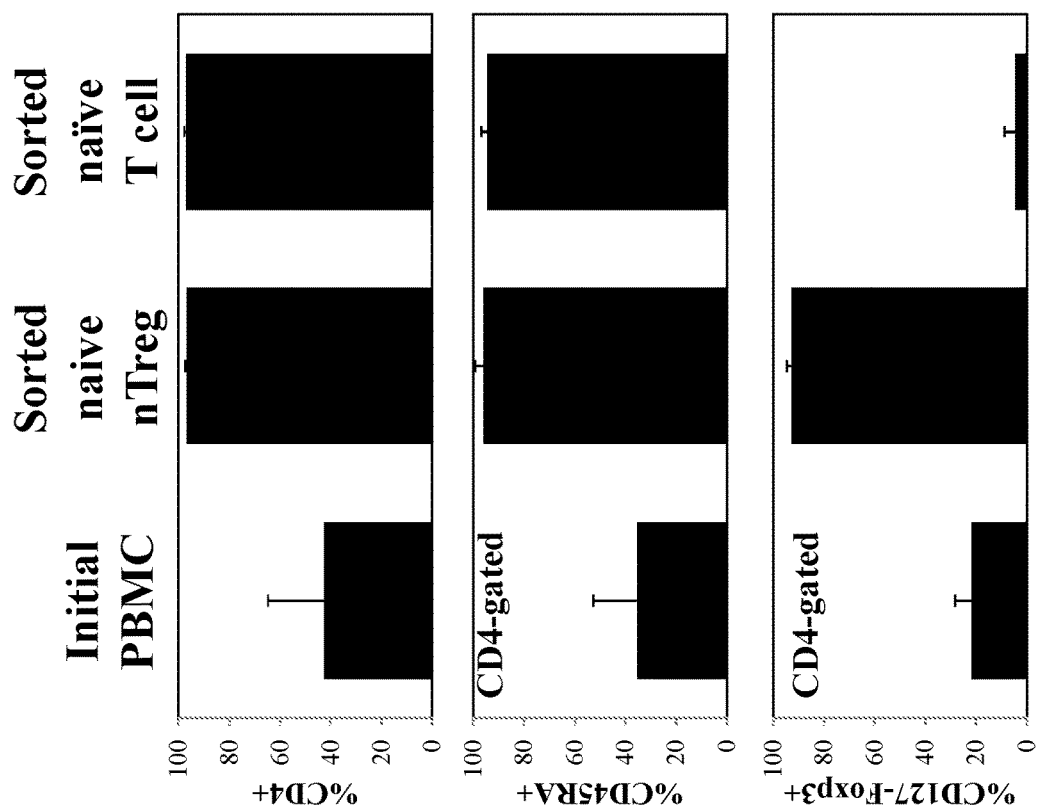
FIG. 2 is a graph showing a post-sort purification summary at day 0 (n=3).

See FIG. 1A for a schematic showing the purification methods described herein and FIG. 1B for an exemplary FACS histogram of the purification scheme. After sorting, naïve tTreg and naïve CD4 T cells were assessed for purity by re-staining for CD4, CD25, CD127, CD45RA and Foxp3. The results are shown in FIG. 2, and indicated that the sorted cells contained ≥97% CD4+ cells, ≥94% CD4RA+ cells, and ≥93% CD127-Foxp3+ cells.

Figure 3:
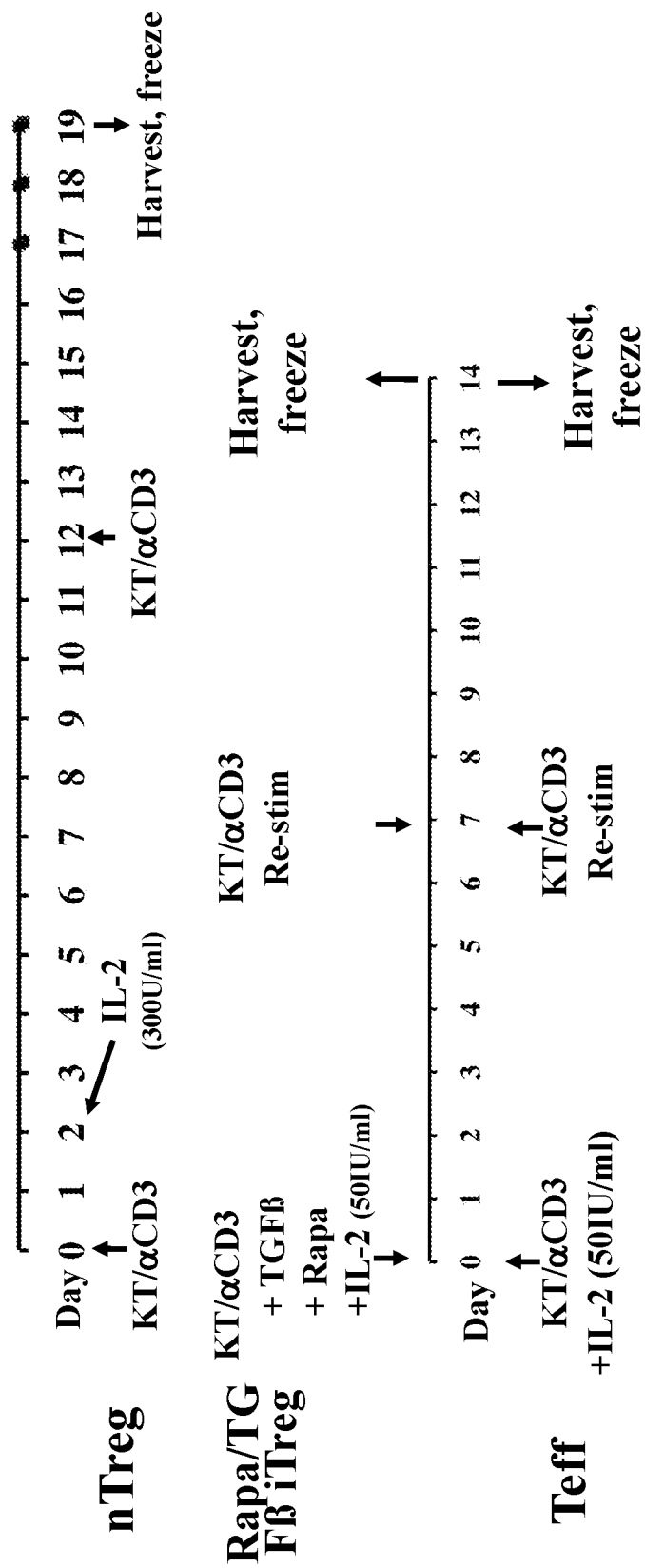
FIG. 3 is a time line of in vitro expansion of naïve tTreg, Rapa/TGFbeta iTreg, and Teff.

In vitro expansion of naïve tTreg, Rapa/TGFβ iTreg and Teff was performed according to the time line shown schematically in FIG. 3. Sorted, naïve tTreg and CD4+ T cells were expanded with anti-CD3 mAb-loaded KT64/86 (as shown in FIG. 1A), media was changed 3× per week, and cells were re-stimulated on day 12 or day 7 (tTreg vs. Rapa/TGFbeta iTreg and Teff, respectively). At the end of the culture period, cells were harvested and frozen in the indicated aliquots.

Specific details are provided below.
Culture Conditions
KT64/86 (fresh, 1:2 KT to Treg)
Cell density: $0.25$-$0.5 \times 10^6$ viable NC/ml
seeding density: $1.6$-$3.2 \times 10^5$ viable cells/cm$^2$
IL2 (300 IU/ml for tTreg; 50 IU/ml for iTreg and Teff): day 2 and w/re-feeding (total media)
Rapa (100 ng/ml) and TGFbeta (10 ng/ml): day 0 and w/re-feeding (fresh media only)
Re-stimulation (keep in IL-2):
KT64/86 (fresh, 1:2 KT to Treg)
Cell density 0.25 M/ml for 7 days, 0.5 M/ml thereafter
Aliquots at Harvest
for us: freeze 5 aliquots of 10 million cells in freezing medium (1 ml each)
FIG. 6: 1 aliquot of RNA from 20e6 cells
FIG. 7B: 1 aliquot of 100 million cells
FACS Analysis: (@, Culture Term)
45RA/LAP/127/25/FoxP3/HLA-DR/45RO/4
19/CTLA-4/127/25/FoxP3/Helios/8/4
27/57/Ki-67/127/28/FoxP3/CCR7/4
Suppression Assay
In vitro CFSE: single assay on frozen/thawed Treg aliquots done at the same time.

Example 2—CLIP and RNA Isolation

Cultured T cells were rinsed once with PBS. The cells were then added to 10 ml PBS/plate (100 mm) and exposed to 400 mJ/cm$^2$ UVA light, followed by an additional 200 ml/cm$^2$ from a UVAR light set (Therakos). The light set was calibrated periodically using a UVX meter fitted with a UVA detector (UVP; Therakos). The cells were collected, washed twice with PBS, and then lysed on ice for 20 minutes in lysis buffer (25 mM Tris-HCl, pH 8.0, 150 mM NaCl, 2 mM MgCl$_2$, 0.5% NP-40, and mM DTT) and a freshly added protease inhibitor cocktail (Pierce), 1 mM PMSF, and 250 U/ml RNasin (Promega). The lysates were then centrifuged at 10,000 g at 4° C. for 10 minutes, and the supernatants were subjected to preclearance by a 60-minute incubation at 4° C. with pre-blocked protein A agarose beads, which were prepared by incubating protein A agarose with salmon sperm DNA (100 μg/ml) and BSA (10 mg/ml) overnight at 4° C. A volume of 400 μl of the protein A agarose beads was added to each tube of cross-linked lysate. Prior to their addition to the lysate, the beads were washed three times with 0.1 M Na phosphate (pH 8.0) prior to the addition of 50 μl of bridge Ab [2.4 mg/ml; donkey anti-rabbit IgG F(c); Abnova]. The tubes were then rotated at room temperature for 60 minutes and washed three times with 0.1 M Na phosphate (pH 8.0). The beads were re-suspended in 400 μl 0.1 M Na phosphate (pH 8.0) prior to the addition of 10 μl of argonaute 2 rabbit mAb (Cell Signaling Technology). The tubes were rotated at 4° C. for 5 hours and washed three times with lysis buffer. The cross-linked and precleared lysate was added to one prepared tube of beads, and the bead/lysate mix was rotated for 4 hours at 4° C. The beads were then washed twice with lysis buffer, three times with lysis buffer containing 900 mM NaCl and 1% NP-40, twice with lysis buffer, and once with lysis buffer containing 0.05% NP-40. After washing, the beads were subjected to DNase treatment by incubation with 250 μl of a DNA digestion solution containing 40 mM Tris-HCl, pH 8.0, 10 mM MgSO4, 1 mM $CaCl_2$), 200 U/ml RNasin, and 0.04 U/ml DNase I (Promega) at 38° C. for 20 minutes, with gentle shaking every 5 minutes. The RNAs caught by CLIP were extracted with either TRIzol LS (Invitrogen), which permits the isolation of total RNA, or an miRNeasy kit (QIAGEN), which is designed for the purification of total RNA, including miRNA and other small RNA molecules.

Example 3—Affymetrix Microarrays and Analyses

The total cellular RNA (tcRNA) was extracted with TRIzol LS reagent from the CLIP agarose beads and cleaned with RNeasy columns (QIAGEN). After the quality of the total RNA was verified by an Agilent 2100 Bioanalyzer, the samples were processed using the WT-Ovation Pico System (Affymetrix), which requires only 500 pg of total RNA and a single round of amplification for samples with even stricter concentration restraints. This system incorporates oligo(dT) and random primers for amplification at the 3' end and throughout the whole transcriptome. Affymetrix human genome U133A Plus 2.0 arrays were used, which contain 47,000 transcripts for annotated genes and expressed sequence.

Example 4—Exiqon miRNA Microarrays and Analyses

Total RNA, including miRNAs and other small RNA molecules, were purified from CLIP agarose beads using the miRNeasy Mini Kit (QIAGEN). After the quality of the total RNA was verified by an Agilent 2100 Bioanalyzer, miRNA microarray experiments were conducted using a single channel for Hy5 on the Exiqon sixth-generation miRCURY LNA miRNA array; these experiments were performed in duplicate. The RNAs and the spike-in miRNAs were treated with calf intestinal alkaline phosphatase (CIP) and then labeled using the Exiqon miRCURY LNA microRNA Array Power Labeling Kit. The denatured, labeled samples were hybridized to miRNA array slides at 56° C. for 16 hours using an Agilent Hybridization SureHyb chamber and gasket slide. The samples were then subjected to a stringent wash protocol. The slides were scanned with a GenePix 4000 microarray scanner (Molecular Devices). The images were captured and analyzed by GAL-file (Exiqon Inc.), which included 1,032 miRNA IDs that had been annotated by miRBase, version 16.0 (microrna.sanger.ac.uk on the World Wide Web). The median of the spot signals after the subtraction of the relative background signals was used as the expression value. The expression levels were calculated using the signals that were above the background level. A probe was retained if the signals in at least half of the samples in at least one condition were 2.5 times above the background signal.

Example 5—Results

Figure 4A:
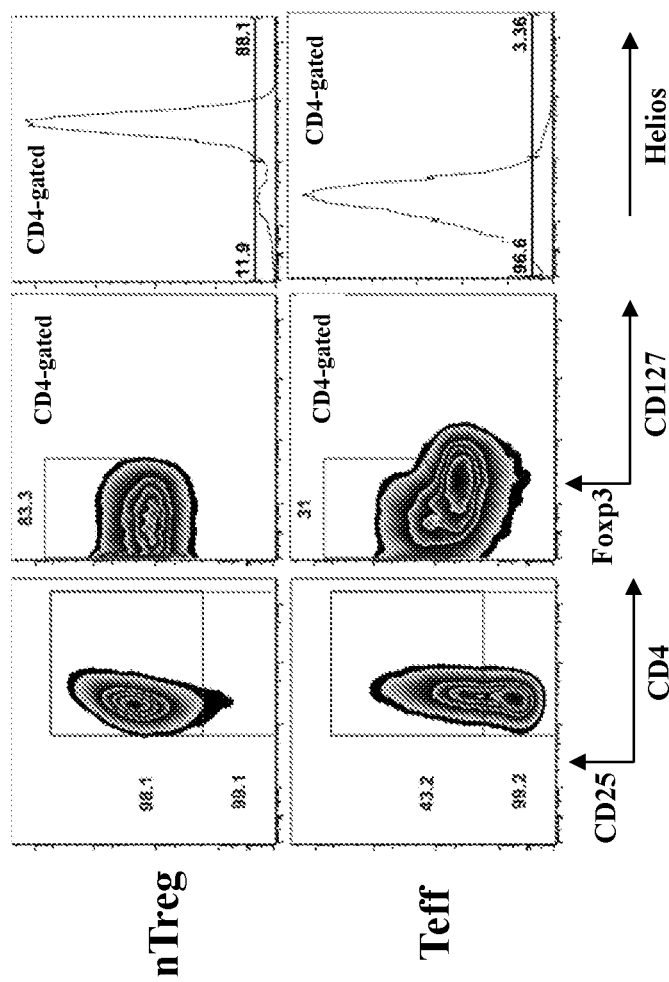
FIG. 4A shows a representative FACS histogram of expanded Treg.
Figure 4B:
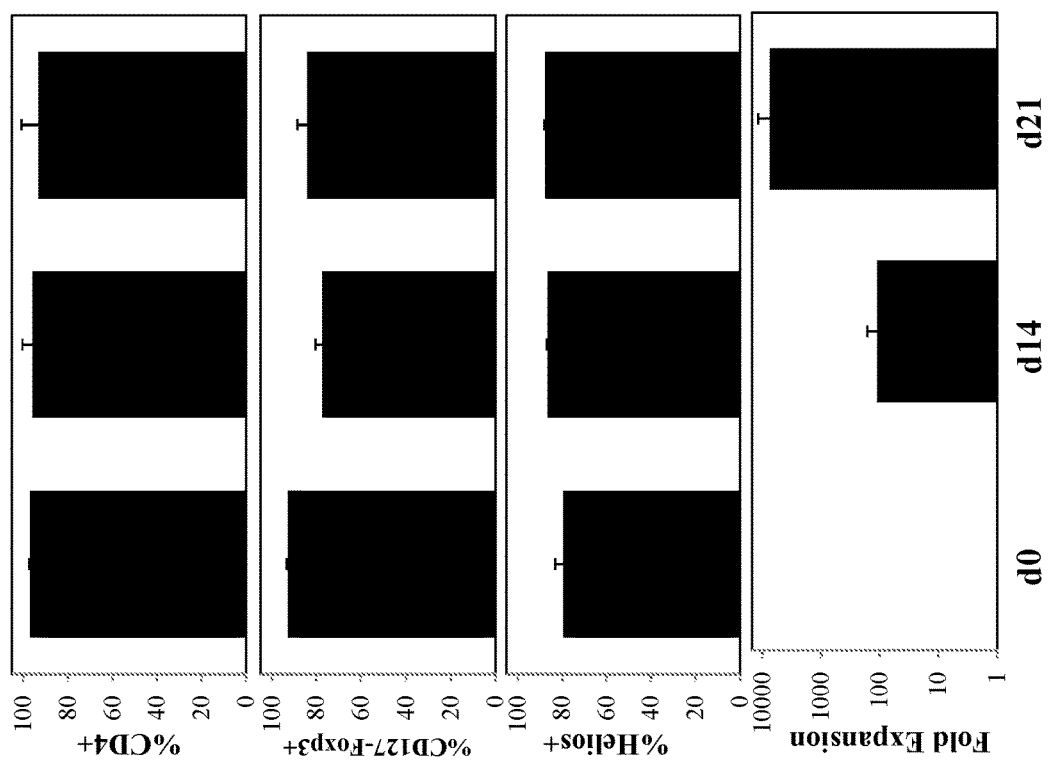
FIG. 4B is a graph showing the fold-expansion of Treg on day 0, day 14 and day 21 (n=3).

At the end of the culture period, tTreg purity was assessed by flow cytometry. FIG. 4A is a representative FACS histogram showing the purity of tTregs, and FIG. 4B is a graph showing the fold expansion of cells on day 0, day 14 and day 21. See, also, Table 1.

TABLE 1

| Final tTreg product | |
| --- | --- |
| % CD4+ | 99 ± 0.4 |
| % CD4+25+ | 91 ± 9 |
| % CD127-Foxp3+ | 84 ± 5 |
| % Helios+ | 88 ± 1 |
| Fold expansion (range) | 7475 ± 4362 (3663-14592) |

Figure 5A:
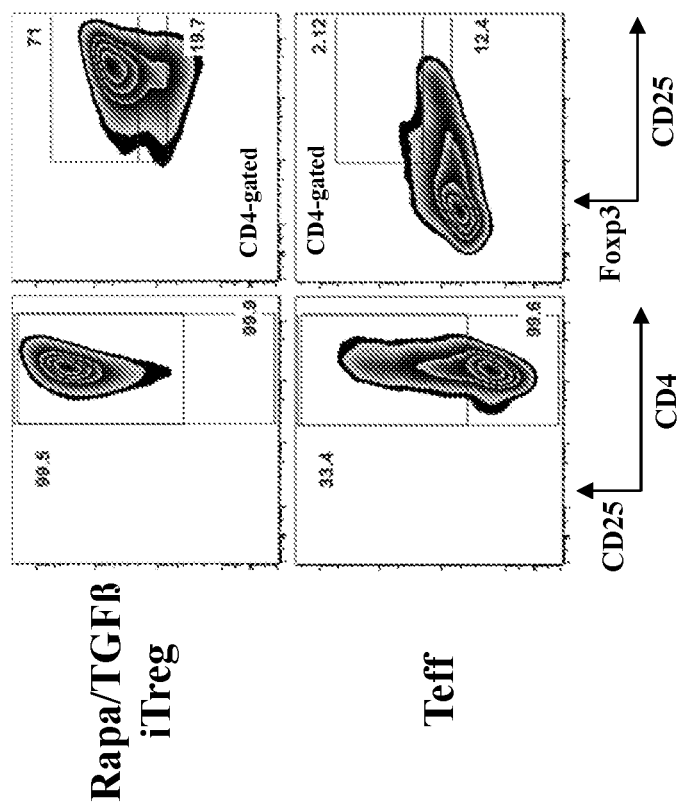
FIG. 5A shows a representative FACS histogram of expanded Rapa/TGFβ iTreg and Teff.
Figure 5B:
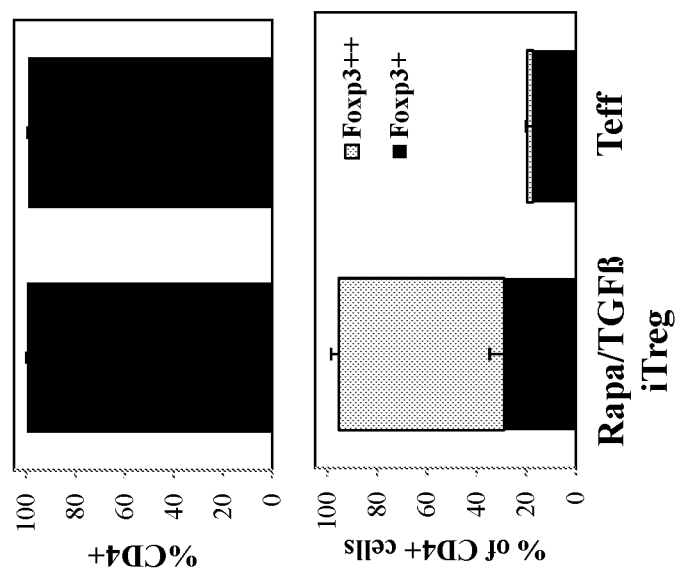
FIG. 5B is a graph showing the fold-expansion of Rapa/TGFβ iTreg and Teff (n=3).

At the end of the culture period, Rapa/TGF beta iTreg and Teff purity was assessed by flow cytometry. FIG. 5A is a representative FACS histogram of expanded Rapa/TGF beta iTreg and Teff, and FIG. 5B is a graph showing the fold expansion of Rapa/TGFbea iTreg and Treff. See, also, Table 2.

TABLE 2

Figure 6:
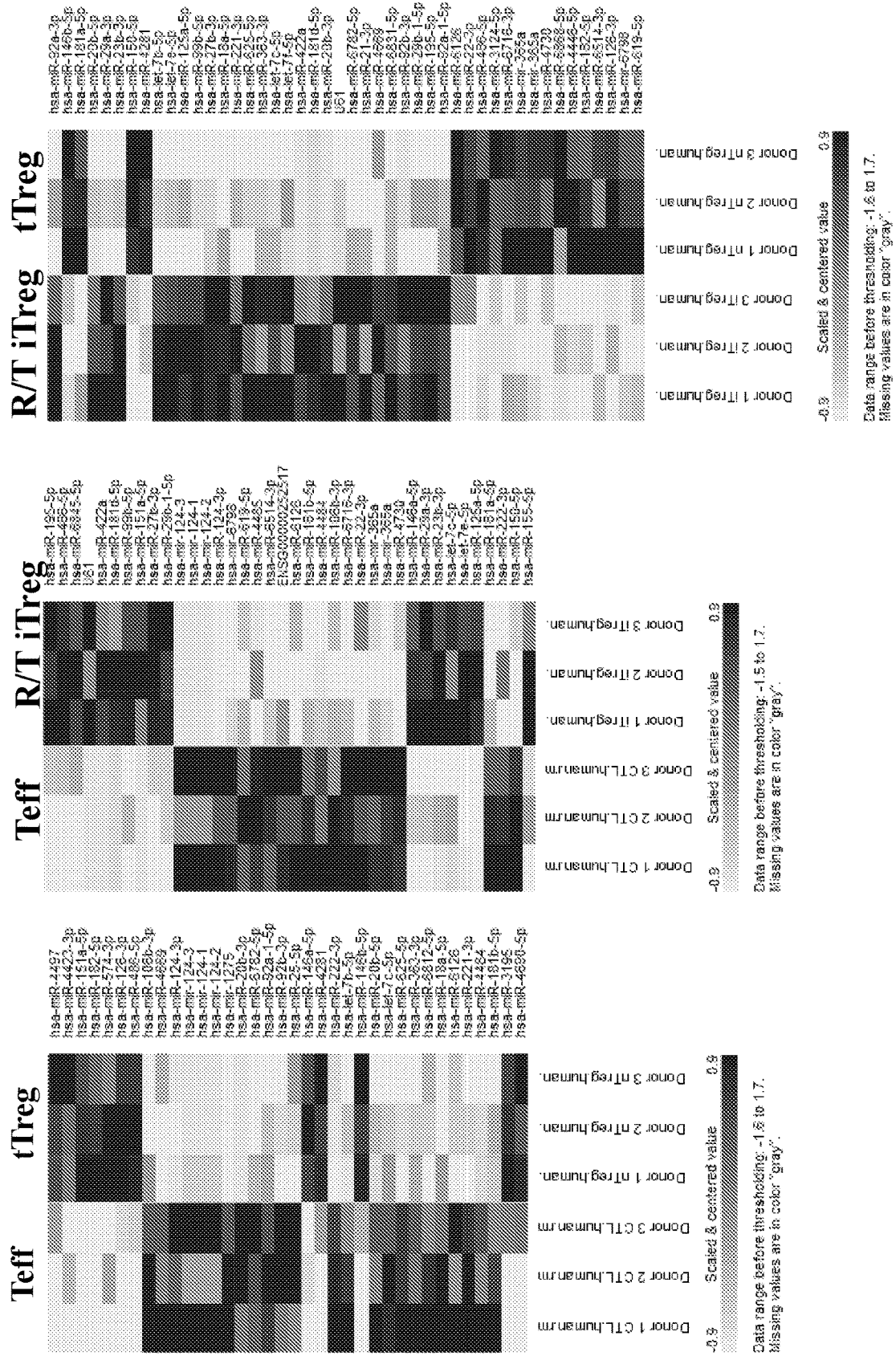
FIG. 6 is a graphical comparison of miRNA expression in tTreg, R/T iTreg and Teff (n=3).

| Final Product | Rapa/TGF beta iTreg | Teff |
| --- | --- | --- |
| % CD4+ | 99 ± 0.2 | 99 ± 0.2 |
| % CD4+25+ | 99 ± 0.2 | 49 ± 15 |
| % Foxp3 (TOTAL) | 95 ± 3 | 20 ± 3 |
| % Foxp3+ | 29 ± 6 | 17 ± 3 |
| % Foxp3++ | 66 ± 3 | 2 ± 0.4 |
| Fold expansion (range) | 1077 ± 539 (575-1955) | 7785 ± 5785 (3042-17232) | miRNA microarrays were used to identify differentially expressed miRNA molecules. miRNA was purified from tTreg, Rapa/TGFβ iTreg and Teff and quantitated by microarray. Differential miRNA expression between tTreg, R/T iTreg and Teff is shown in FIG. 6.

Figure 7A:
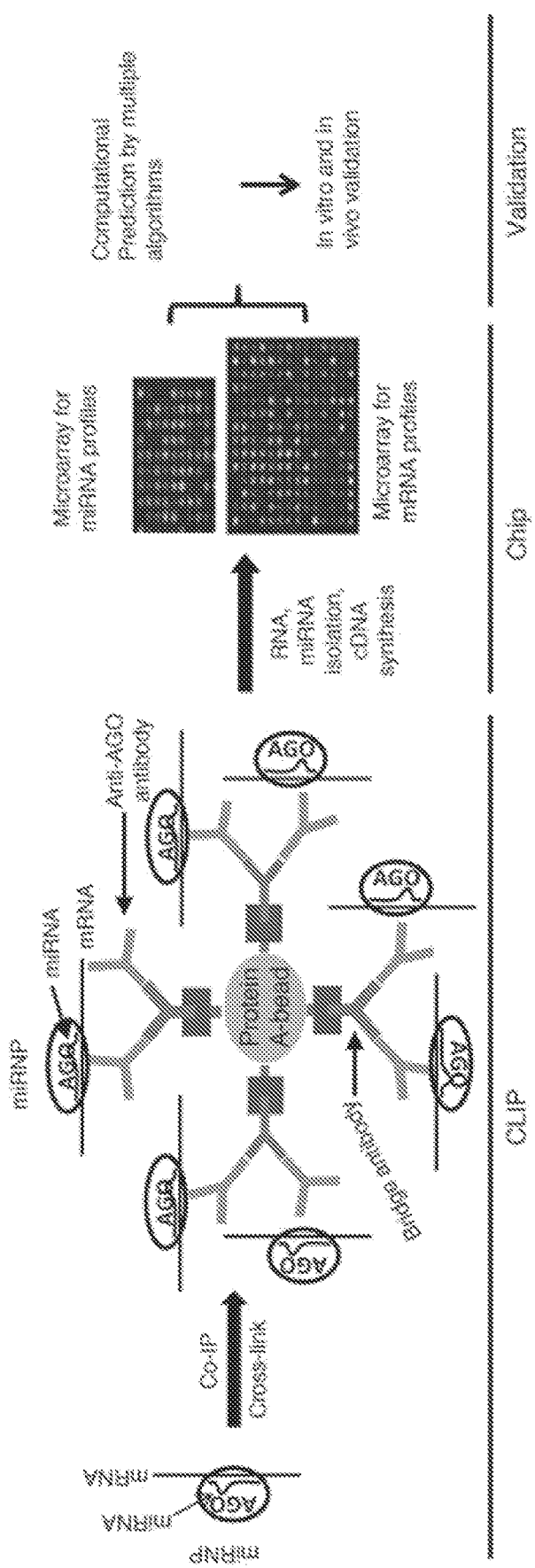
FIG. 7A is a schematic illustration of the enrichment profiles of miRNAs and their targets using AGO-CLIP-ChIP.

After CLIP, the miRNAs were co-immunoprecipitated with anti-AGO2 antibodies and then bound to the bridge antibody, anti-rabbit IgG F(c), which links to the protein A agarose beads. The miRNAs and the target mRNAs that associated with the AGO protein were processed using Exiqon miRNA and Affymetrix Gene 430.2 microarrays. This high-throughput assay can screen direct and legitimate miRNA targets in a genome-wide manner and can be used to identify a miRNA-mediated gene regulation network. FIG. 7A is a schematic illustration (adapted from Sun et al., 2013, J. Clin. Invest., 123(11):4739-54) of the enrichment profiles of miRNAs and their targets using AGO-CLIP-ChIP, and FIG. 7B provides the mRNA CLIPChIP profiles of the tTreg, Rapa/TGFβ iTreg and Teff cells.

Example 6—List of miRNAs

Table 3 below shows the list of miRNAs and the results in an analysis of pairwise significance between Teff and each type of Treg cells. In addition, publications previously describing a role for specific miRNA moieties in Foxp3+ iTreg or tTreg are referenced.

TABLE 3

| miRNA | Pairwise significant (lower, higher) | iTreg | tTreg |
|---|---|---|---|
| miR-18a-5p | (tTreg, Teff), (tTreg, iTreg) | | |
| miR-20b-3p | (tTreg, iTreg) | | |
| miR-22-3p | (iTreg, Teff), (iTreg, tTreg) | | |
| miR-23b-3p | (Teff, iTreg), (tTreg, iTreg) | | |
| miR-24-2-5p | (Teff, tTreg) | | |
| miR-25-5p | (tTreg, Teff) | | |
| miR-27b-3p | (Teff, iTreg), (tTreg, iTreg) | | |
| miR-29a-3p | (Teff, iTreg), (tTreg, iTreg) | | |
| miR-29b-3p | (Teff, iTref) | | |
| miR-29b-1-5p | (Teff, iTreg), (tTreg, iTreg) | | |
| miR-30e-5p | (Teff, tTreg) | | |
| miR-92a-1-5p | (tTreg, Teff) | | |
| miR-92a-3p | (tTreg, iTreg) | | |
| miR-92b-3p | (tTreg, Teff) | | |
| miR-92b-5p | (Teff, tTreg) | | |
| miR-99b-5p | (Teff, iTreg), (tTreg, iTreg) | | |
| miR-106b-3p | (tTreg, Teff) | | |
| miR-124-1 | (iTreg, Teff), (tTreg, Teff) | | |
| miR-124-2 | (iTreg, Teff), (tTreg, Teff) | | |
| miR-124-3p | (iTreg, Teff), (tTreg, Teff) | | |
| miR-124-3 | (iTreg, Teff), (tTreg, Teff) | | |
| miR-125a-3p | (Teff, tTreg) | | |
| miR-125a-5p | (Teff, iTreg), (tTreg, iTreg) | | Li et al., 2015, Sci Rep, 5: 14615 |
| miR-126-3p | (Teff, tTreg), (iTreg, tTreg) | Qin et al., 2013, J. Cell Mol Med, 17(2): 252-64 | Qin et al., 2013, J. Cell Mol Med, 17(2): 252-64 |
| miR-146a-5p | (Teff, tTreg) | | Lu et al., 2010, Cell, 142: 914-29; Bhairavabhotla et al., 2015, Hum Immunol., 77: 201-13 |
| miR-146b-5p | (Teff, tTreg), (iTreg, tTreg) | | Bhairavabhotla et al., 2015, Hum Immunol., 77: 201-13 |
| miR-150-5p | (iTreg, Teff), (iTreg, tTreg) | | |
| miR-151a-5p | (Teff, iTreg) | | |
| miR-181a-5p | (iTreg, Teff) | | |
| miR-181d-5p | (Teff, iTreg) | | |
| miR-181b-5p | (iTreg, Teff) | | |
| miR-181a-2-3p | (Teff, iTreg); (Teff, tTreg) | | |
| miR-182-5p | (Teff, tTreg), (iTreg, tTreg) | Bothur et al., 2015, Nat Comm, 6: 8576 | Chen et al., 2014, BMC Cancer, 14: 489; Kelada et al., 2013, PLoS Path, 9: e1003451 |
| miR-195-5p | (Teff, iTreg), (tTreg, iTreg) | | |
| miR-221-3p | (tTreg, Teff), (tTreg, iTreg) | | |
| miR-222-3p | (tTreg, Teff) | | |
| miR-324-3p | (Teff, tTreg) | | |
| mir-365a | (iTreg, Teff), (iTreg, tTreg) | | |
| miR-422a | (Teff, iTreg), (tTreg, iTreg) | | |
| miR-423-5p | (Teff, tTreg), (Teff, iTreg) | | |
| miR-486-5p | (Teff, iTreg), (Teff, tTreg), (iTreg, tTreg) | | |
| miR-574-3p | (Teff, tTreg) | | |
| miR-619-5p | (iTreg, Teff) | | |
| miR-625-5p | (tTreg, Teff), (tTreg, iTreg) | | |
| mir-1275 | (tTreg, Teff) | | |
| miR-4281 | (Teff, tTreg), (iTreg, tTreg) | | |
| miR-4484 | (iTreg, Teff), (tTreg, Teff) | | |
| miR-4497 | (Teff, tTreg) | | |
| miR-4669 | (tTreg, Teff) | | |
| miR-4730 | (iTreg, Teff), (iTreg, tTreg) | | |
| miR-6126 | (iTreg, Teff), (iTreg, tTreg) | | |
| miR-6514-3p | (iTreg, Teff) | | |
| miR-6716-3p | (iTreg, Teff), (iTreg, tTreg) | | |
| miR-6782-5p | (tTreg, Teff), (tTreg, iTreg) | | |
| mir-6798 | (iTreg, Teff), (iTreg, tTreg) | | |
| miR-6812-5p | (tTreg, Teff) | | |
| let-7b-5p | (tTreg, iTreg) | | |
| let-7c-5p | (tTreg, iTreg) | | |
| let-7e-5p | (Teff, iTreg), (tTreg, iTreg) | | |

Example 7—Treatment of tTregs and CD4+ T-Cells tTreg and CD4+ T-cell cultures, generated as described herein, were frozen on days 14 and 7, respectively. Frozen cells were thawed and re-stimulated with anti-CD3/CD28 mAb-coated Dynabeads (Life Technologies, Carlsbad, Calif.) at 1:3 (cell to bead) ratios in the presence of recombinant IL-2. After 6 days, cultures were washed, re-suspended at $1\times10^6$ cells/ml, and nanoparticle-encapsulated RNA (50 nM; Scramble/Antagomir, Table 4: EXIQON, Woburn, Mass.) or TRAF6 inhibitor (8 Darmstadt, Germany) or NF-kB inhibitor (PS-1145, 3 µM or 6 Millennium Pharmaceuticals, Cambridge, Mass.) were added. DMSO were vehicles and used as controls. Cells were cultured another 2 days without further manipulation, and were harvested and assayed as listed. For some experiments, tTreg were kept in culture longer (as indicated) without further antagomir addition.

TABLE 4

Sequences of Scramble, Antagomir and RNU44

| Name | Sequences |
|---|---|
| Scramble | TAA CAC GTC TAT ACG CCC A (SEQ ID NO: 1) |
| Antagomir | AGC CTA TGG AAT TCA GTT CTC (SEQ ID NO: 2) |
| RNU44 | CCU GGA UGA UGA UAG CAA AUG CUG ACU GAA CAU GAA GGU CUU AAU UAG CUC UAA CUG ACU (SEQ ID NO: 3) |

Example 8—Mice

NOD/SCID/gamma c−/− mice were purchased from The Jackson Laboratory (Bar Harbor, Me.), and housed in a specific pathogen-free facility in micro-isolator cages. Mice were used at 8-12 weeks. Animal protocols were approved by IACUC at the University of Minnesota.

Example 9—Cell Purification and Culture

For all experiments, non-mobilized peripheral blood (PB) leukapheresis products were purchased from Memorial Blood Center (St. Paul, Minn.). Naïve human PB tTreg (CD4$^+$25$^+$127$^-$45RA$^+$) were sort-purified from PB mononuclear cells (PBMNCs) (Ficoll-Hypaque, Amersham Biosciences) in a two-step procedure in which CD25+ cells were initially enriched from PBMNCs by AutoMACS (PosselD2) with GMP grade anti-CD25 microbeads (Miltenyi Biotec). CD25high cells were stained with CD4, CD8, CD25, CD127 and CD45RA and sorted via FACSAria as CD4+, CD8−, CD25high, and CD127−CD45RA+. Note that the bead-bound and fluorochrome-conjugated anti-CD25 antibodies recognize different epitopes (Miltenyi Biotec), followed by sorting on a FACSAria (BD Biosciences). Naïve human CD4 T-cells were sort-purified from the CD25-fraction as CD4+25-127+45RA+.

Purified naïve tTreg and CD4 T-cells were stimulated with a K562 cell line engineered to express CD86 and the high-affinity Fc receptor (CD64) (37) (2:1 tTreg/KT), which had been irradiated with 10,000 cGy and incubated with anti-CD3 mAb (Miltenyi Biotec). In some experiments, tTregs were stimulated with KT64/86 cells that were pre-loaded, irradiated, and frozen (1:1 tTreg/KT). Naive tTreg and CD4 T-cells were cultured in X-Vivo-15 (BioWhittaker, Walkersville, Md.) media supplemented with 10% human AB serum (Valley Biomedical). Recombinant IL-2 (300 IU/mL for Treg, 50 IU/mL for control T-cells; Chiron, Emeryville, Calif.) was added on day 2 and maintained for culture duration. Cultures were maintained at $0.25\times10^6$ to $0.5\times10^6$ viable nucleated cells/ml every 2 to 3 days.

Example 10—Flow Cytometry, ImageStream and Antibodies

Human-specific antibodies used for flow cytometry included: CD4 (RPA-T4), CD8 (RPA-T8), CD25 (M-A251), CD45RA (HI100), IFN-gamma, IL-17a, annexin V (PE), 7-AAD (FITC) were purchased from BD Pharmingen, while Foxp3 (clone 249D) was obtained from BioLegend and Ki67 from eBioscience. For cytokine analysis, cells were pre-treated by PMA, ionomycin and brefeldin A for 6 hours and then stained by different cytokine antibodies. The annexin V (PE)/7-AAD (FITC) were applied to assess the apoptosis of tTreg. Acquisition was performed using a LSRII (BD Bioscience) and data were analyzed using FlowJo software (TreeStar) or IDEA (Admin). Nuclear localization of NF-kB was quantitated using an imaging flow cytometer (Imagestream, Amnis Corp; Seattle, Wash.) by intracellularly staining tTreg with anti-NF-kB (vendor) and, after washing, incubating with DRAQS for 15 minutes at 10 µM final concentration.

Example 11—Anti- and Pro-Apoptotic Gene Expression Analysis and TAQMAN® Low Density Arrays (TLDAs)

RNA was extracted from cell pellets using RNeasy Mini Kit with on-column DNase digestion (Qiagen; Hilden, Germany). cDNA synthesis was performed as described in the Expression Analysis Technical Manual (Affymetrix; Santa Clara, Calif.). GAPDH was used as control gene and related gene expression (Bcl-2, Mcl-1, Bcl-xL, BID and BAX; all from IDT, Coralville, Iowa), was analyzed on an Applied Biosystems 7500 Real-Time PCR System using Taqman Universal PCR Master Mix #4304437 and Assay on Demand primer/probe kits (Applied Biosystems; Waltham, Mass.). For TLDA assay, TLDA v2.0 was performed on the 7900HT real-time PCR system (Applied Biosystems) according to the manufacturer's protocol. Average delta CT was acquired from the results for further analysis. PCR cycling conditions were performed as follows: 95° C. for 15 s and 60° C. for 1 min, 40 cycles and then 95° C. for 10 min. To normalize RNA input, Human RNU44 (Table 4) small RNA was used as an internal control.

Example 12—miRNA Target Prediction and Luciferase Reporter Assay

Potential miRNA targets were sorted by utilizing miRNA prediction software TargetScan (targetscan.org on the World Wide Web), MIRDB (mirdb.org on the World Wide Web) and microRNA (microrna.org on the World Wide Web). For the luciferase reporter assay, the pGL3 firefly luciferase reporter plasmids with the wild-type or mutated (mut) 3' UTR sequences of TRAF6 (Table 5) were transiently transfected into HEK293 cells along with 25 nM miR-146b-5p precursor or negative control precursor and a Renilla luciferase reporter for normalization. After two days, the luciferase activities were measured by QT-PCR. Based on the cells transfected by pGL3 control vector, the mean of the results was set as 100%. The data are mean and standard deviation (SD) of separate transfections.

TABLE 5

Wild Type and Mutated 3'UTR Sequences of TRAF6

| Name | Sequences |
|---|---|
| Wild | CTTCAGTCTTTTTGTAGTATTATATGTAATATATTAAAAGTGAA AATCACTACCGCCTTGTGCTAGTGCCCTCGAGAAGAGTTATTGC TCTAGAAAGTTGAGTTCTCATTTTTTTAACCTGTTATAGATTTC AGAGGATTTGAACCATAATCCTTGGAAAACTTAAGTTCTCATTC ACCCCAGTTTTTCCTCCAGGTTGTTACTAAGGATATTCAGGGAT GAGTTTAAACCCTAAATATAACCTTAATTATTTAGTGTAAACAT GTCTGTTGA (SEQ ID NO: 4) |
| Mut | CTTCAGTCTTTTTGTAGTATTATATGTAATATATTAAAAGTGAA AATCACTACCGCCTTGTGCTAGTGCCCTCGAGAAGAGTTATTGC TCTAGAAAGTTGCTGGAGACTTTTTTTAACCTGTTATAGATTTC AGAGGATTTGAACCATAATCCTTGGAAAACTTACTGGAGACTTC ACCCCAGTTTTTCCTCCAGGTTGTTACTAAGGATATTCAGGGAT GAGTTTAAACCCTAAATATAACCTTAATTATTTAGTGTAAACAT GTCTGTTGA (SEQ ID NO: 5) |

Predicted miR-146b binding sequence is underlined

Example 13—Suppression Assays

The in vitro-suppressive capacity of expanded tTregs was assessed with a carboxy fluorescein succinimidyl ester (CFSE) inhibition assay as previously published (Hippen et al., Blood, 2008, 112(7):2847-57). Briefly, PBMNCs were purified, labeled with CFSE (Invitrogen), and stimulated with anti-CD3 mAb-coated beads (Dynal)±cultured tTreg (1:2 to 1:32 tTregs/PBMNCs). On day 4, cells were stained with antibodies to CD4 and CD8, and suppression was determined from the Division Index (FlowJo, TreeStar). nTregs suppressed CD4 and CD8 T cell responses equivalently and only CD8 data are presented.

Example 14—Xenogeneic GVHD Model

A published xenogeneic GVHD model was used (Hippen et al., Sci. Transl. Med., 2011, 3(83):83ra41). Briefly, NOD/Scid/γc−/− mice between 8-12 weeks old were housed in a pathogen-free facility in micro-isolator cages. On day 0, mice were irradiated with 50 cGy. Human PBMNCs ($15 \times 10^6$) were injected with or without expanded tTregs ($15 \times 10^6$). To document PBMC-associated peripheral T-cell expansion, animals were bled (10-40 µL), red blood cells lysed, and tTreg and PBMC subsets were enumerated by flow cytometry by staining with mAbs to human CD4, Foxp3, CD8, CD45, and HLA-A2 (to differentiate between PBMC and tTreg) and acquired with a known number of counting beads (Sigma-Aldrich). Mice were assessed for signs of GVHD daily, weighed thrice weekly, and human cells in blood quantitated by flow cytometry on the specified dates.

Example 15—Statistical Analyses

RT-PCR data were analyzed using SDS v2.3 software. Survival data were analyzed using Prism 5 (Mantel-Cox). Other data were analyzed by analysis of variance (ANOVA) or Student t test. Probability (P) values less than or equal to 0.05 were considered statistically significant.

Example 16—Identification of Human tTreg-Specific miRNA

Figure 8:
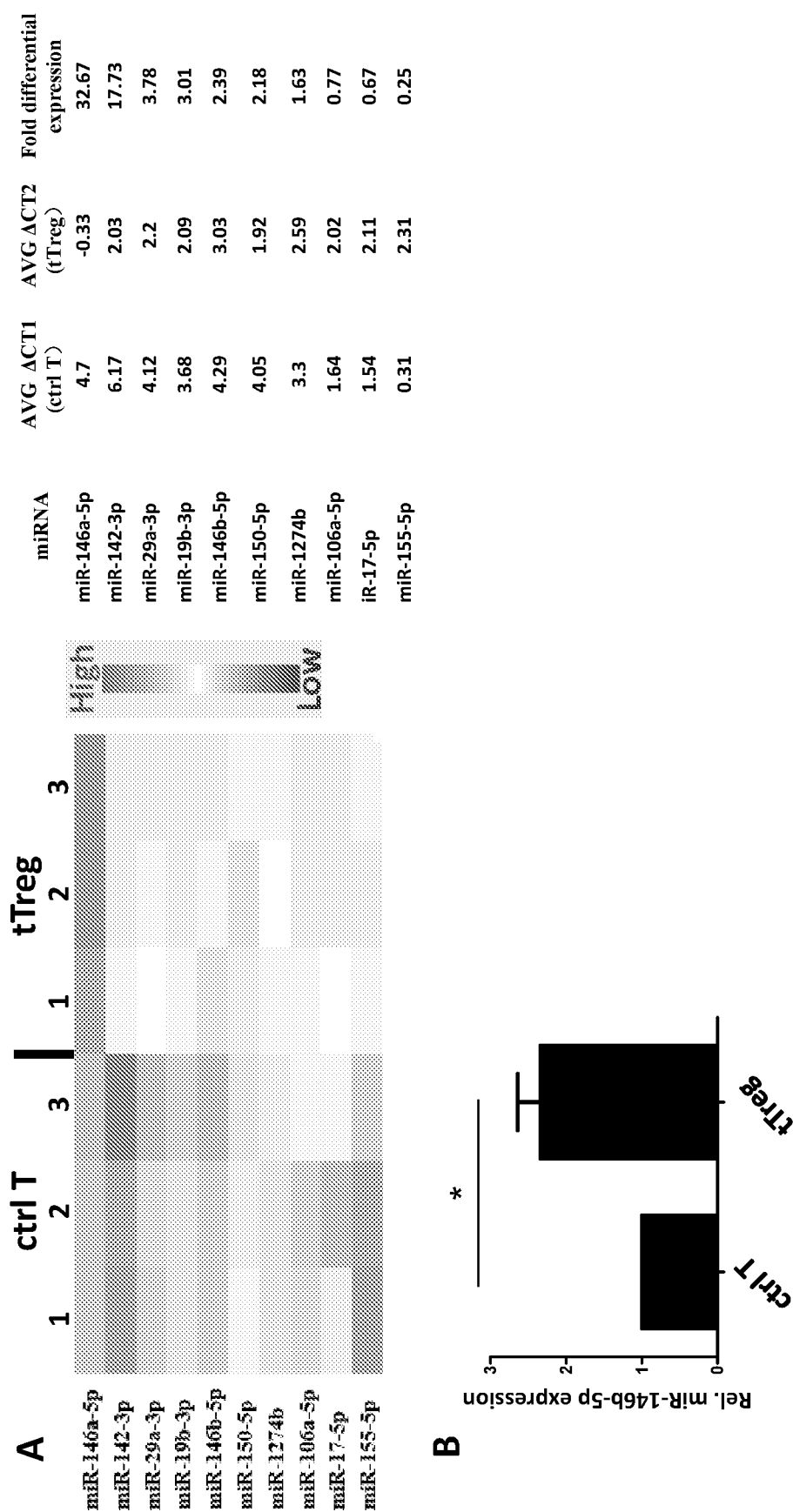
FIG. 8 is data showing that miRNA profiling of expanded naïve CD4+ T-cells and naïve tTreg cells demonstrates stronger expression of miR-146b in human tTreg cells (n=3). Naïve T cells (CD4+25-127+45RA+) and naïve tTreg (CD4+25+127-45RA+) were sort-purified and expanded in vitro. miRNA expression in control T cells (Ctrl T) and tTreg was determined by miRNA Taqman Low-Density Array (TLDA). Panel A shows, after analyzing 768 miRNAs, the top 10 differential miRNAs between tTreg and Ctrl T were gated for further analysis by heatmap (left panel) and fold differential expression (right panel) ($P<0.05$). Panel B is a graphs showing that differential expression of miR-146b in Ctrl T and tTreg cells (n=3) was confirmed by RT-PCR elative ($P<0.05$).

Changes in miRNA expression are observed during T-cell differentiation (Monticelli et al., Genome Biol., 2005, 6(8): R71). To identify potential human tTreg-specific miRNA, miRNA expression was compared between in vitro expanded naïve, CD4 T-cells ($CD4^+25^-127^+45RA^+$; control T cells) and naïve, tTregs ($CD4^+25^{++}127^-45RA^+$). TLDA was utilized to reveal differential miRNA expression between human naïve tTregs and CD4 T-cells. RNU44, a ubiquitously expressed small nucleolar RNA, was used to normalize expression between the cell types. After analyzing 768 miRNAs by ranking fold expression, the top 10 differential miRNAs between tTreg and CD4 T cells were chosen for further analysis (FIG. 8A). Two miRNAs, which were preferentially expressed (>10.0 fold) in tTreg cells (miR-146a-5p and miR-142-3p), have been implicated in tTreg development and/or function. miR-146a-5p has proved to be essential for Treg development, phenotype and function, while miR-142-3p negatively regulates tTreg suppressive function by restricting the AC9/cAMP pathway (Lu et al., Cell, 2010, 142(6):914-29; Huang et al., EMBO Rep., 2009, 10(2):180-5; Okoye et al., PNAS USA, 2014, 111(30): E3081-90; Zhao et al., Cancer Res., 2010, 70(12):4850-8). Four miRNAs (miR-29a-3p, miR-19b-3p, miR-150-5p and miR-146b-5p), which had differential expression >2.0 fold, also have known functions in tTreg; miR-29a and miR-150 promote Treg differentiation, while miR-19b negatively regulates Treg induction from naïve T cells (de Candia et al., Front Immunol., 2014, 5:43; Singh et al., J. Immunol., 2015, 195(12):5667-77; Jiang et al., Blood, 2011, 118(20):5487-97; Gomez-Rodriguez et al., J. Exp. Med., 2014, 211(3): 529-43; Warth et al., EMBO J., 2015, 34(9):1195-213).

miR-146b-5p required deeper investigation. While some reports found miR-146a-5p positively regulates tTreg function in mice (Lu et al., Cell, 2010, 142(6):914-29), others found miR-146a and/or 146b knock-down had no impact on human Treg function (Bhairavabhotla et al., Hum. Immunol., 2016, 77(2):201-13). Therefore, it was hypothesized that miR-146b-5p might have an opposite role in controlling tTreg function compared to miR-146a-5p. To confirm the higher expression in tTreg cells, differential expression of miR-146b-5p was validated by quantitative qRT-PCR (FIG. 8B).

Figure 9:
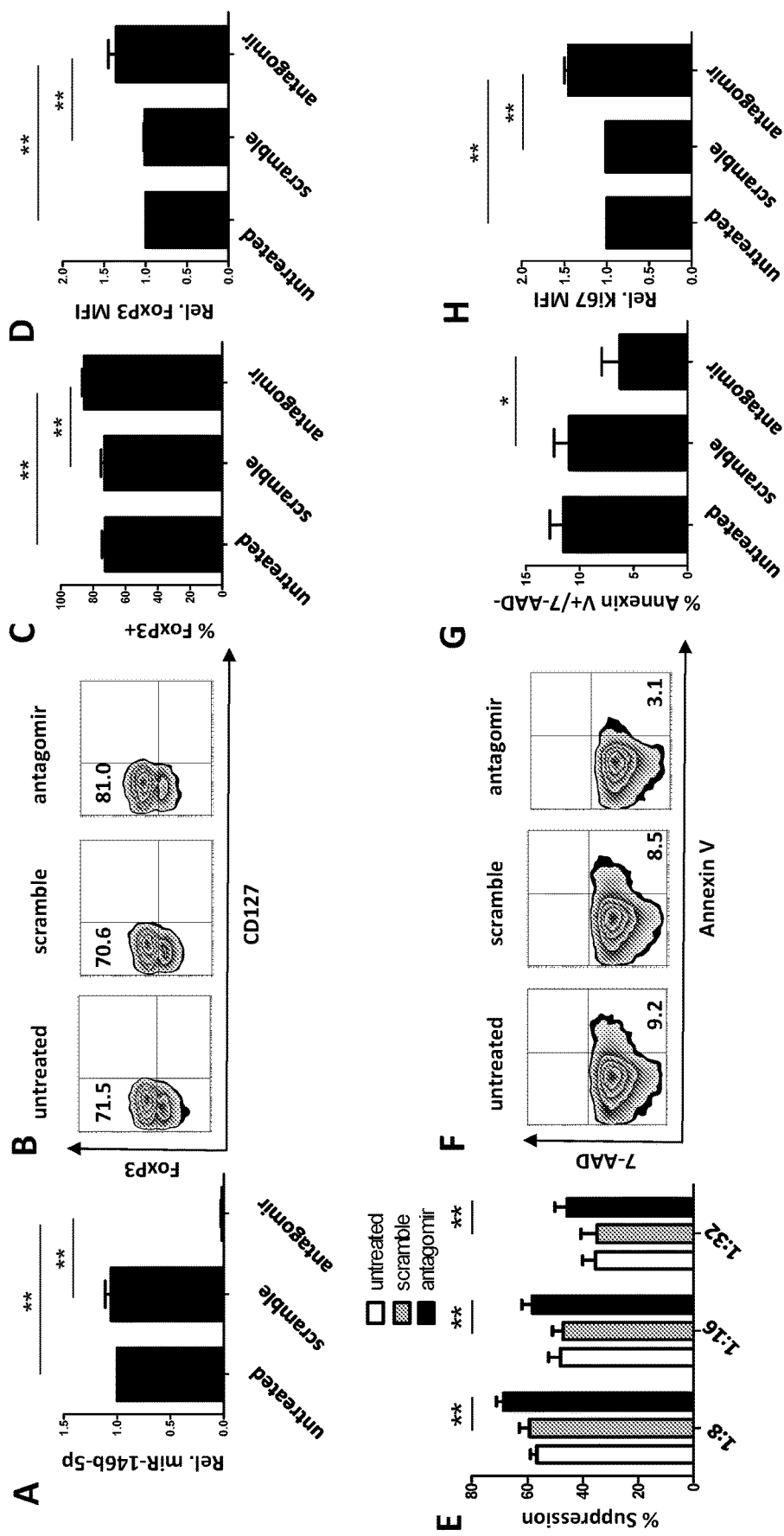
FIG. 9 is data demonstrating that tTreg cells treated with miR-146b-5p antagomir show increased FoxP3, Ki67 expression and viability with enhanced suppressive function. Naïve PB tTregs were sort purified, expanded in vitro, treated with or without scramble/antagomir for the final two days of culture. Panel A is a graph showing that miRNA was purified from each culture and miR-146b expression was assessed by RT-PCR to determine knockdown efficiency (n=3). Panel B are representative examples of gating (on CD4+ cells) for Foxp3 vs. CD127 staining on tTreg treated with antagomir compared to untreated and scramble groups. Summary of overall % Foxp3+CD127- cells. Panel C is a graph showing the level of Foxp3 expression, and Panel D is a graph showing the level of Foxp3 expression in tTreg from each group (n=5). Panel E is a graph showing the percent suppression of in vitro, anti-CD3-mediated CD8+ T cell proliferation at ratios from 1:8 to 1:32 (tTreg:PBMC) as determined by CFSE dye dilution (n=5). Panel F are representative flow images and Panel G is the corresponding statistical analysis of apoptosis tests performed to analysis the survival ability in vitro; it was determined that viability was significantly enhanced after antagomir treatment (n=3). Panel H is a graph showing that higher relative Ki67 MFI level was found after treatment with the antagomir (n=5). Values indicate mean±SEM of these experiments (*$P<0.05$ and **$P<0.01$).
Figure 15:
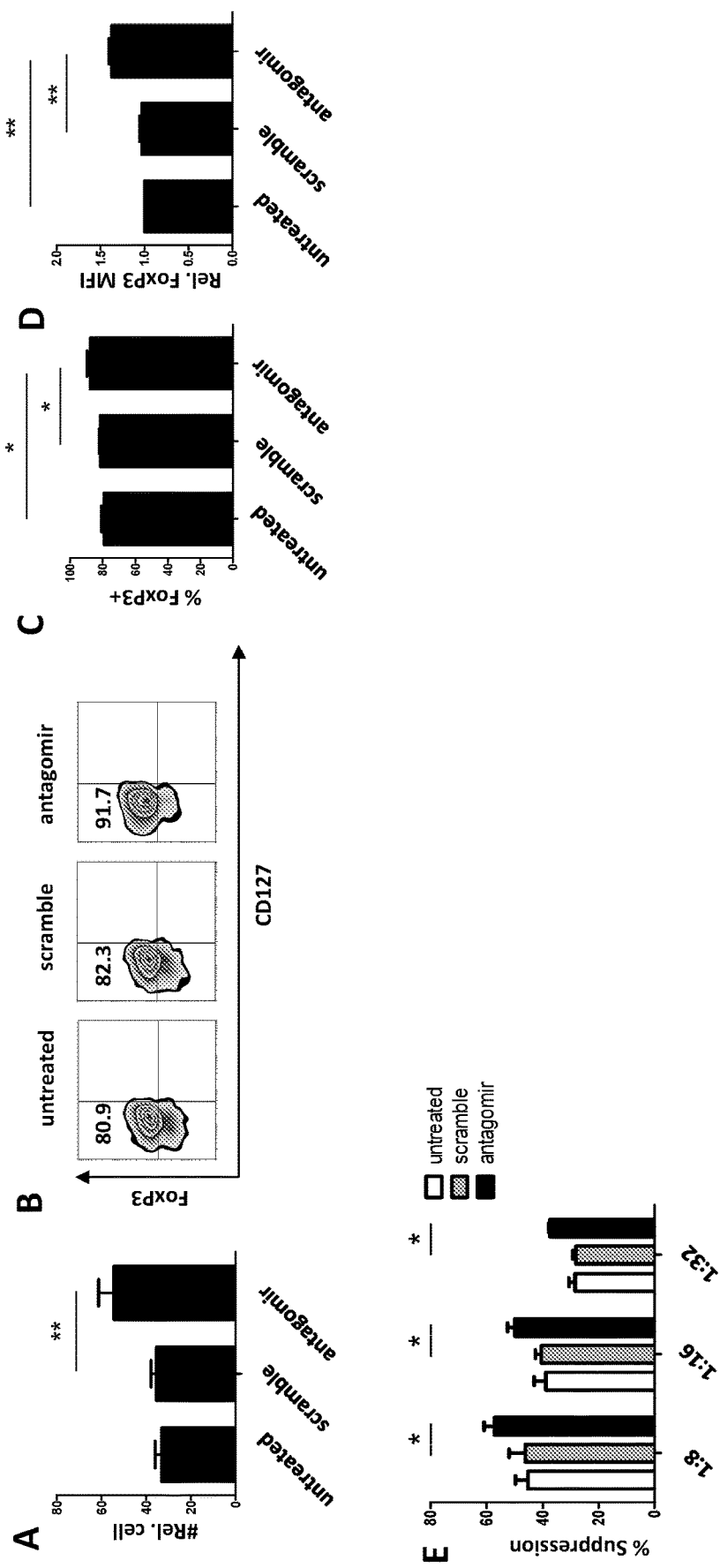
FIG. 15 is data showing that the miR-146b antagomir effects on tTreg are durable, and lead to increased yield while maintaining increased Foxp3 expression. Naïve PB tTreg were sort purified, expanded in vitro and were either left untreated, or were incubated with scramble RNA or miR-146b antagomir. To assess longer-term effects, cultures were maintained for 8 days (instead of 2) following a single treatment with antagomir (n=3). Panel A is a graph showing the relative fold expansion of tTreg groups following treatment. A representative example (Panel B) and a summary (Panel C) of flow cytometry assessing markers of tTreg purity following treatment with scramble/antagomir for 8 days. Panel D is a graph showing Foxp3 expression levels in tTreg from each group after 8 days. Panel E is a graph showing percent suppression of in vitro, anti-CD3-mediated CD8+ T cell proliferation at ratios from 1:8 to 1:32 (tTreg:PBMC) as determined by CFSE dye dilution. Values indicate mean±SEM of these experiments (*P<0.05 and **P<0.01).

Example 17—Knock-Down of miR-146b-5p Enhances FoxP3 Expression, Viability, Expansion and Suppressive Function In Vitro To determine whether miR-146b-5p affected human tTreg phenotype or suppressive function, tTregs were incubated with nanoparticle-encapsulated miR-146b-5p antagomir as described in the methods. Scrambled miRNA was utilized as a control. miR-146b-5p knockdown efficiency was ≥95% (FIG. 9A) as assessed by qRT-PCR. Knock-down of miR-146b-5p in tTreg cells increased Foxp3 protein expression at the population (85.5%±3.5% vs 73.1%±4.6%, P<0.05, FIG. 9B, 9C) and per-cell level (FIG. 9D) compared to scrambled group. The in vitro suppressive function of untreated tTregs also was compared with those treated with scrambled or miR-146b-5p antagomir. Using a CFSE-based proliferation assay with tTreg:PBMC ratios from 1:8 to 1:32, antagomir treatment was found to significantly enhance tTreg suppressive function at each tTreg:PBMC (peripheral blood mononuclear cell) ratio tested (FIG. 9E), with ~2-fold increase in efficacy (i.e. antagomir-treated tTreg at 1:16 were as suppressive as scramble-treated at 1:8). One previous study suggested that CD4 T-cells from miR-146b (but not miR-146a) transgenic mice were significantly impaired in their ability to expand in response to in vitro TCR stimulation, due to a combination of increased apoptosis and a defective entrance into S phase (Burger et al., Blood, 2014, 123(26): 4089-100). Therefore, it was tested whether miR-146b-5p antagomir treatment would have an impact on in vitro tTreg expansion. Although no significant difference in expansion was observed during the initial 2 day treatment period, antagomir-treated tTreg cultures showed increased viability and staining for Ki-67, a marker of proliferation (FIG. 9F-9H). Cultures were continued without further antagomir treatment to assess long-term cell accumulation. By day 8 post treatment, antagomir-treated tTreg had expanded significantly more than untreated tTreg or those treated with scrambled RNA (FIG. 15A). Effects of antagomir-treatment were durable, as miR-146b expression was still reduced 70% on day 8 (not shown) and treated tTreg maintained their higher Foxp3 expression and suppressive function (FIG. 15B-15E). Therefore, knock down of miR-146b-5p favors FoxP3 expression, expansion, suppressive function and attenuates apoptosis protein.

Figure 16:
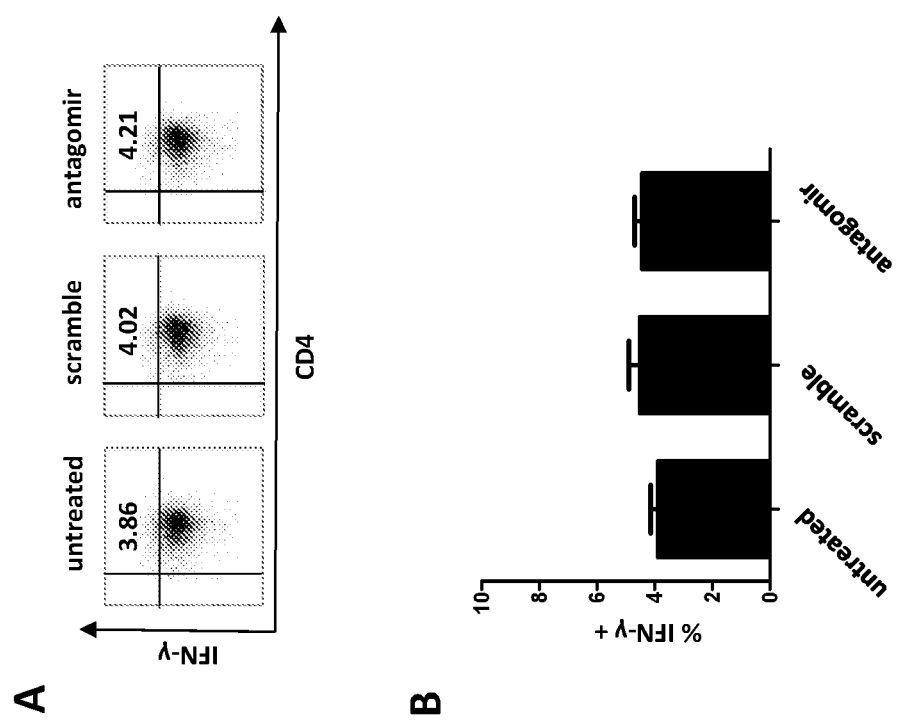
FIG. 16 is data showing that antagomir treatment does not cause an increase in the number of tTreg secreting IFN-gamma. In vitro expanded tTreg were treated the final 2 days with nothing, scramble RNA or miR146b antagomir. IFN-gamma secreting cells were determined by intracellular cytokine assay following re-stimulation with PMA and Ionomycin. A representative flow analysis (Panl A) and a summary (Panel B) of the % IFN-gamma+ cells in treated tTreg cultures. Values indicate mean±SEM of three independent experiments.
Figure 17:
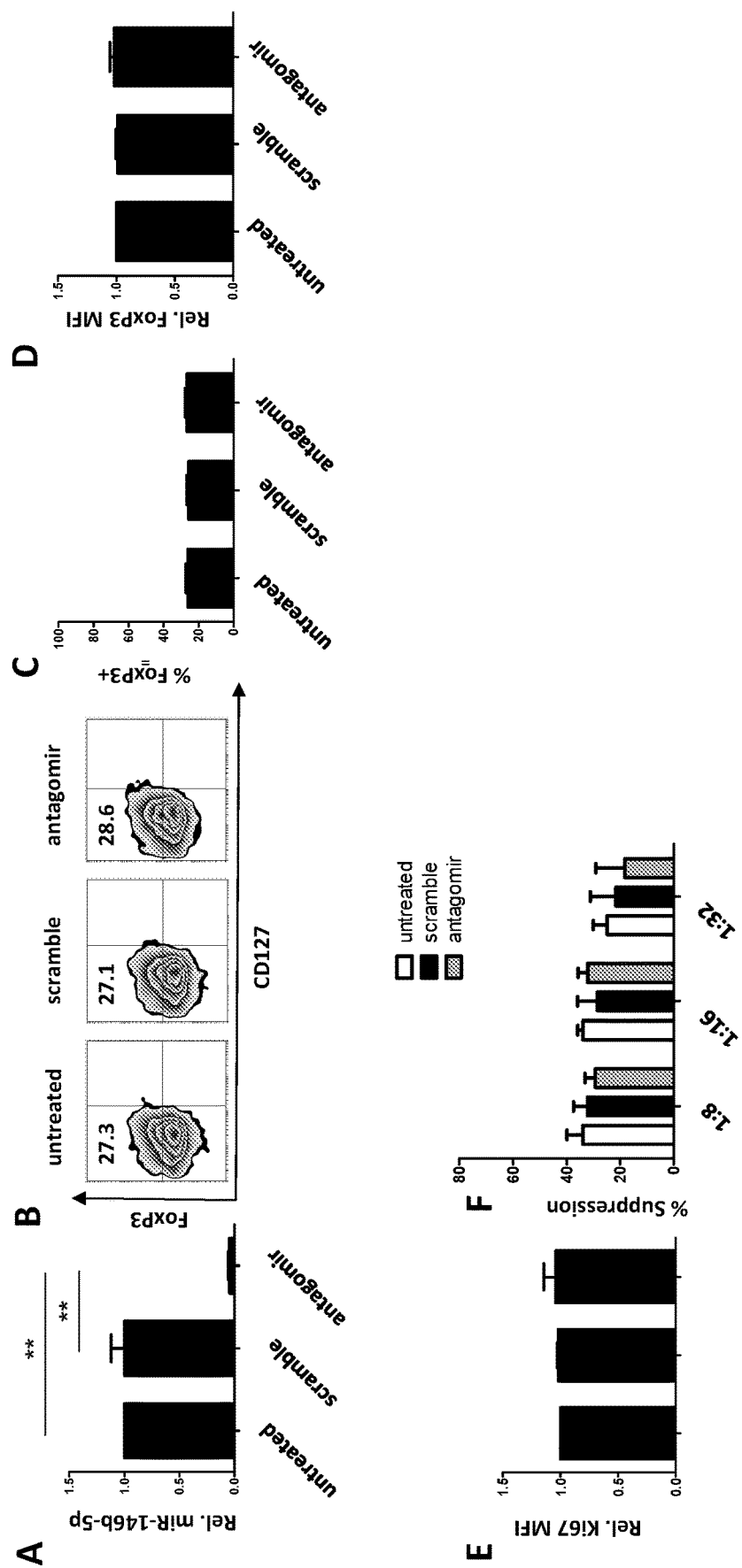
FIG. 17 is data showing that miR-146b-5p antagomir treatment of control T-cells does not induce FoxP3 expression or suppressive function. Naïve PB CD4 T-cells (CD4+ 25-127+45RA+) were sort-purified, expanded in vitro, and treated with nothing, scramble or antagomir for 2 days (n=3). Panel A is a graph showing that miRNA was purified from each culture and miR-146b expression was assessed by RT-PCR to determine knockdown efficiency. Panel B shows a representative example of Foxp3 vs. CD127 staining on control T-cells treated with antagomir compared to untreated and scramble groups (gated on CD4+ cells). A summary of overall % Foxp3+CD127− cells (Panel C) and level of Foxp3 expression (Panel D) in T-cells from each group. Panel E is a graph showing Ki67 expression after antagomir treatment. Panel F is a graph showing the percent suppression of in vitro, anti-CD3-mediated CD8+ T-cell proliferation at ratios from 1:8 to 1:32 (T cell:PBMC) as determined by CFSE dye dilution. Values indicate mean±SEM of these experiments (*P<0.05 and **P<0.01).

Previous murine studies suggested that miR-146a-5p was involved in Th1 responses and its deficiency led to dysregulated IFN-gamma production (Lu et al., Cell, 2010, 142(6): 914-29; Stickel et al., Blood, 2014, 124(16):2586-95). However, few expanded human tTregs expressed IFN-gamma under these conditions, and expression was not affected by miR-146b-5p antagomir treatment (FIG. 16). Since control CD4 T-cells also expressed miR-146b-5p, albeit at low levels, it was possible that down-modulation of this miRNA would induce Foxp3 expression and suppressive function. Naïve CD4 T-cells were purified, expanded in vitro using conditions similar to those in the original array study, and treated with miR-146-5p antagomir for the final 2 days. miR-146b antagomir treatment had no effect on FoxP3 expression or suppressive function in control CD4 T-cells (FIG. 17). It was hypothesized that the lack of an effect of miR-146b antagomir on conventional T cells is likely due to low miR-146b expression, perhaps related to a lack of Foxp3-mediated miR-146b expression. Alternatively, this difference could be due to the fact that TCR signaling, including TRAF6 and NF-kB activation, is known to be differentially controlled in conventional T cells compared to tTreg. In FIG. 17, no increase in suppressive function was observed. However, a low level of suppression was observed in all Teff cultures. This most likely was due to competition for the stimulatory anti-CD3 beads, especially since the in vitro expanded Teff cells were already in cycle and were physically larger (and thus express more TCR) than the T cells present in the directly ex vivo PBMC cultures. These data indicate that knock-down of miR-146b-5p in human tTregs, but not control CD4 T-cells, increases FoxP3 expression and suppressive function in vitro without increasing IFN-gamma production.

Figure 10:
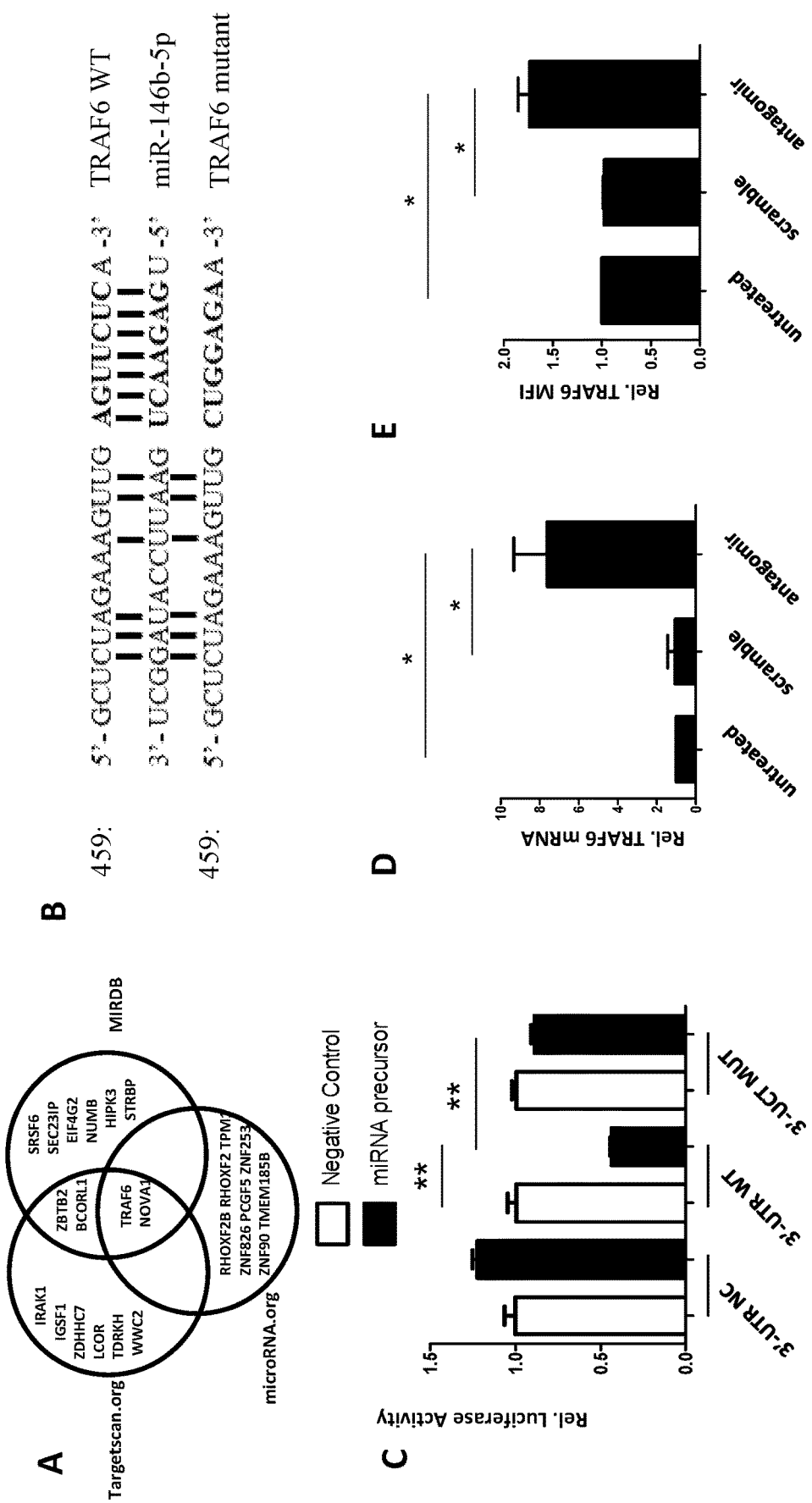
FIG. 10 is data from experiments showing that TRAF6 is a direct target of miR-146b-5p and knock-down of miR-146b-5p increased TRAF6 expression in human tTreg cells (n=3). To assess whether human miR-146b-5p targets TRAF6, HEK293 cells were transduced with plasmids carrying wild type (WT) or mutant (MUT) 3'UTR sequences from TRAF6 linked to a luciferase reporter gene. Cells were also transfected with a Renilla luciferase reporter construct for normalization. Panel A is a schematic showing the three software programs (targetscan.org, MIRDB and microRNA.org) that were utilized to predict the potential target mRNAs of miR-146b-5p, TRAF6, was involved in tTreg function with highest possibilities. Panel B is a schematic representation of the miR-146b-5p target sequence within the 3'UTR of TRAF6. Two nucleotides (complementary to nucleotides 6 and 8 of miR-146b-5p) were mutated in the 3' UTR of TRAF6. The numbers indicate the positions of the nucleotides in the reference wild-type sequences. Panel C is a graph showing the activity of the luciferase gene linked to the wild type (WT) or mutant (MUT) 3'UTR of TRAF6. Luciferase activities were measured after 48 hr. The mean of the results from the cells transfected by control vector was set as 100%. The data are mean and standard deviation (SD) of separate transfections (n=3). Naïve PB tTreg were sort-purified, expanded in vitro, and were treated ±miR-146b antagomir or scrambled RNA as previously described. After treatment, cultured cells were assessed for TRAF6 mRNA and protein expression by RT-PCR or flow cytometry (Panel D and Panel E, respectively). Values indicate mean±SEM of these experiments. (*$P<0.05$ and **$P<0.01$).
Figure 18:
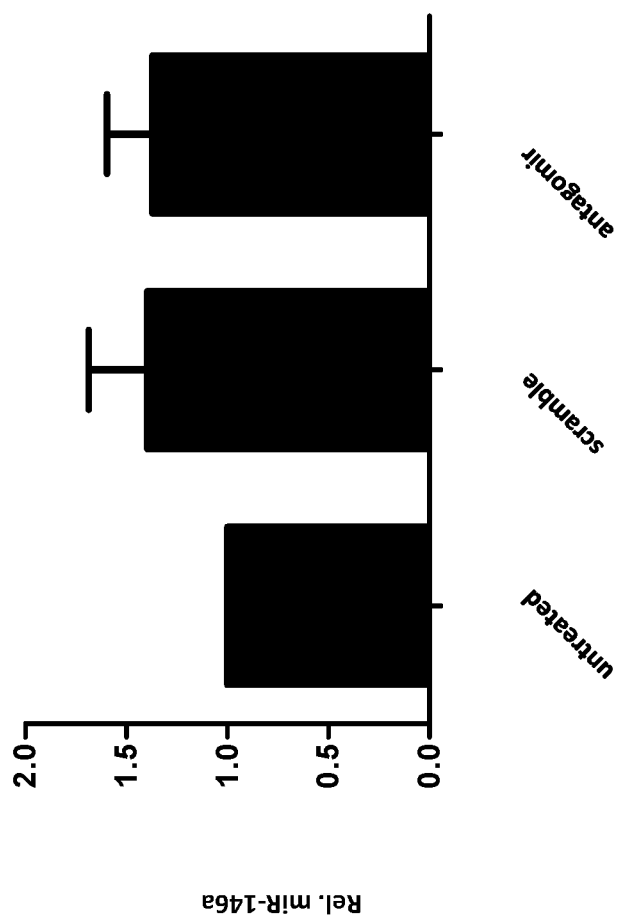
FIG. 18 is a graph showing miR-146b-5p antagomir treatment does not affect the expression of family member miR-146a. In vitro expanded tTreg were treated the final 2 days with nothing, scramble RNA or miR146b antagomir. Cultures were harvested, RNA purified, and miR-146a expression quantitated by qRT-PCR. Values indicate mean±SEM of three independent experiments.
Figure 19:
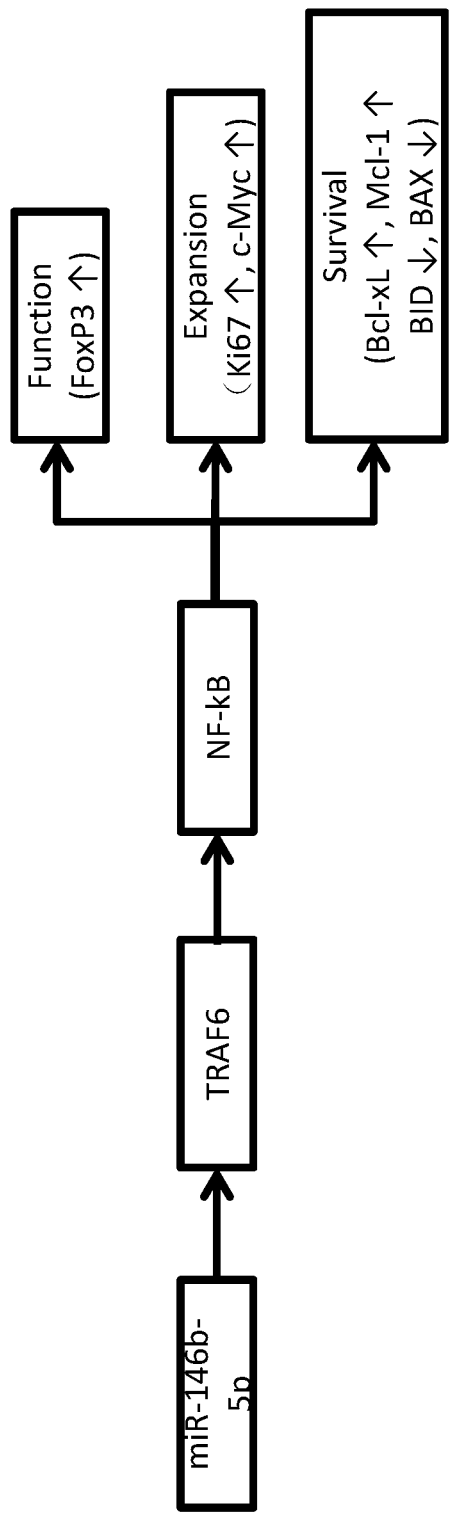
FIG. 19 is a schematic showing the miR-146b-5p—to—TRAF6—to—NF-kB pathway control of tTreg function.

Example 18—TRAF6 is a Direct Target of miR-146b-5p and Knock-Down of miR-146b-5p Increases TRAF6 Expression in Human tTregs To identify potential miR-146b targets, miRNA prediction software (targetscan.org, MIRDB and microRNA.org) was utilized to reveal the potential targeted miRNAs. After sorting top ten predicted miRNAs in each software, it was found that TRAF6 was the one mRNA involved tTreg function with highest possibility (FIG. 10A). Both sets of software identified potential miR-146b-5p binding sites (7-nucleotide) in the 3' UTR of TRAF6 (FIG. 10B). Consistent with this hypothesis, TRAF6 expression was decreased in miR-146b transgenic mice (Burger et al., Blood, 2014, 123(26):4089-100), and inversely correlated with miR-146b-5p expression in umbilical vein endothelial cells (HUVECs) and dendritic cells (DCs) (Park et al., J. Biol. Chem., 2015, 290(5):2831-41; Echavarria et al., Cardiovasc. Res., 2015, 106(3):465-77). To confirm the predicted miR-146b-5p binding site in TRAF6, HEK293 cells were transiently transfected with pGL3 firefly luciferase (ff-luc) reporter plasmids with no insert, or with the wild-type (WT) or mutated (MUT) 3' UTR sequences of TRAF6 (Table 5), along with 25 nM miR-146b-5p or negative control RNA. As shown in FIG. 10C, co-incubation of control RNA or miR-146b did not show a significant difference (P=0.07). While co-incubation of control RNA with WT 3'UTR-tagged ff-luc had no effect, co-incubation with miR-146b resulted in a 60% decrease in ff-luc activity (middle panels). Furthermore, the specificity of this interaction was confirmed because miR-146b did not significantly decrease ff-luc activity in HEK293 cells expressing the mutant 3'UTR (right lanes). While miR-146a and miR-146b are separate gene products, they share a homologous seed region. Since miR-146a can also target TRAF6, it was analyzed miR-146a expression following miR-146b antagomir treatment by qRT-PCR to assess knockdown specificity. The data demonstrated that miR-146a expression in tTreg treated with miR-146b-5p antagomir was similar to those treated with scramble RNA (FIG. 18).

It was next asked whether miR-146b-5p antagomir treatment affected TRAF6 expression in expanded tTregs. FIG. 10D shows that, while no effect was observed in the scramble group, tTregs treated with miR-146b-5p antagomir had significantly higher TRAF6 mRNA expression. In accordance with mRNA level, antagomir treatment significantly enhanced TRAF6 protein expression in tTregs compared to the untreated or scramble-treated groups (FIG. 10E). Taken together, these results show that TRAF6 is a direct target of miR-146b-5p in human tTreg cells.

Figure 11:
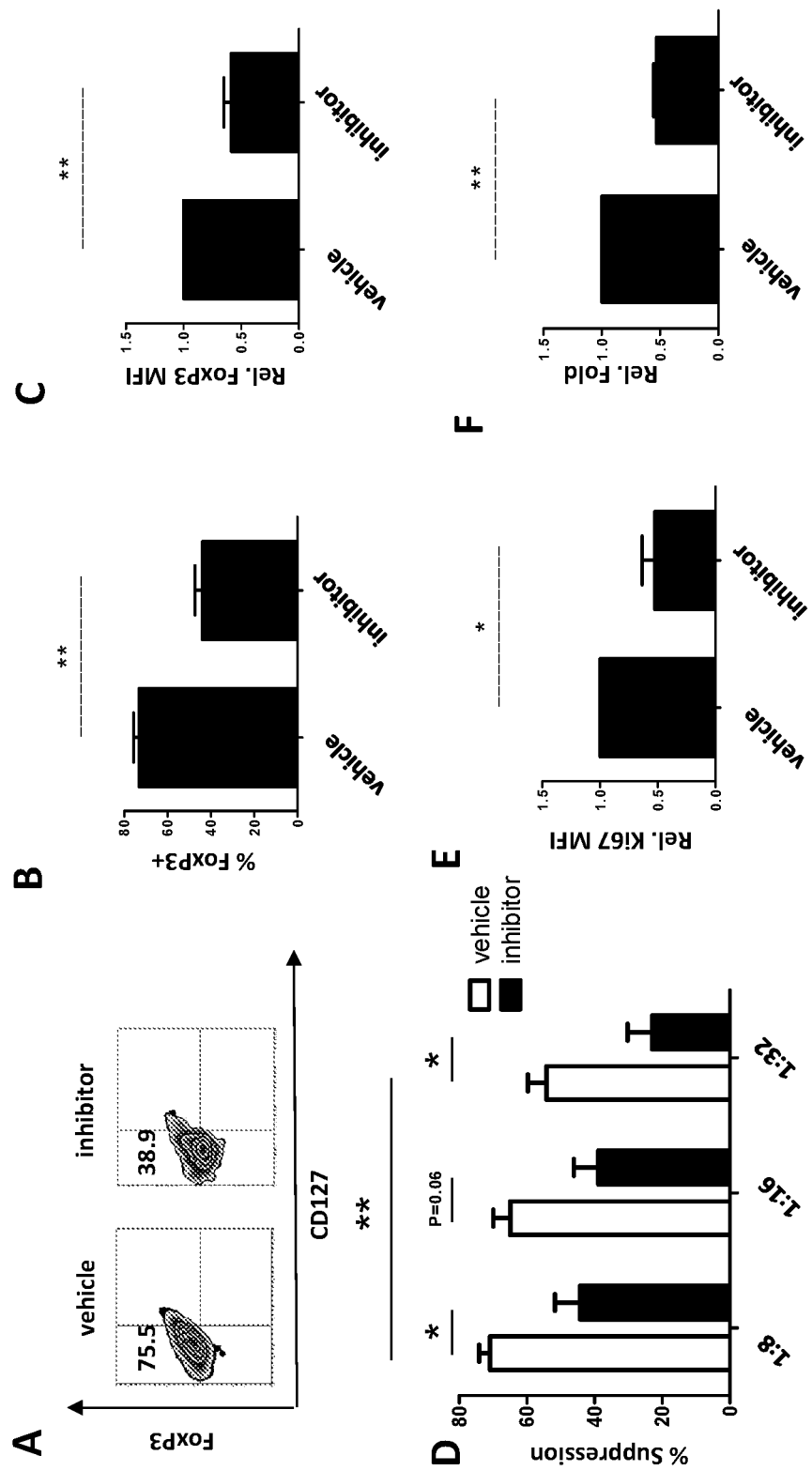
FIG. 11 is data showing that inhibition of TRAF6 signaling impairs human tTreg expansion, Foxp3 expression and suppressive function. tTreg cells were treated with TRAF6 inhibitor for 2 days (n=5). Panel A are representative flow figures of FoxP3+ tTreg in different groups, showing that TRAF6 was significantly decreased after treatment with the inhibitor. FoxP3+ population (Panel B) and expression (Panel C) was measured in these groups, and the inhibitor-treated group was clearly decreased. Panel D is a graph from a CFSE assay performed to measure the suppressive ability, which did show decreased suppressive function at 1:8 and 1:32. Values indicate mean±SEM of these experiments. Panel E is a graph of Ki67 expression measured in these groups, in which the inhibitor-treated group was clearly decreased. Panel F is a graph showing relative folder expansion after inhibitor treatment. (*P<0.05 and **P<0.01).

Example 19—Inhibition of TRAF6 Signaling Impairs Human tTreg Expansion, Foxp3 Expression and Suppressive Function Conditional knockout (cKO) of TRAF6 in murine Treg resulted in decreased Foxp3 stability and loss of in vivo suppressive function (Muto et al., PLoS One, 2013, 8(9): e74639). It was sought to determine if TRAF6 plays a similar role in human tTreg. In vitro expanded tTreg were treated with a TRAF6 signaling inhibitor (6877002) (Chatzigeorgiou et al., PNAS USA, 2014, 111(7):2686-91) for the final 2 days of culture. Similar to reports for murine tTreg, inhibition of TRAF6 signaling in human tTreg cultures decreased Foxp3 protein expression both at a population (68.0%±6.6% vs 46.8%±6.8%, P<0.05, FIGS. 11A and 11B) and individual (FIG. 11C) cell basis compared to vehicle group. Suppressive function was markedly down-regulated after inhibitor treatment (FIG. 11D). TRAF6 inhibitor also decreased proliferative ability (as assessed by Ki-67 staining) after 2 days of treatment, and significantly decreased cell number after 8 days of treatment (FIGS. 11E and 11F).

Figure 12:
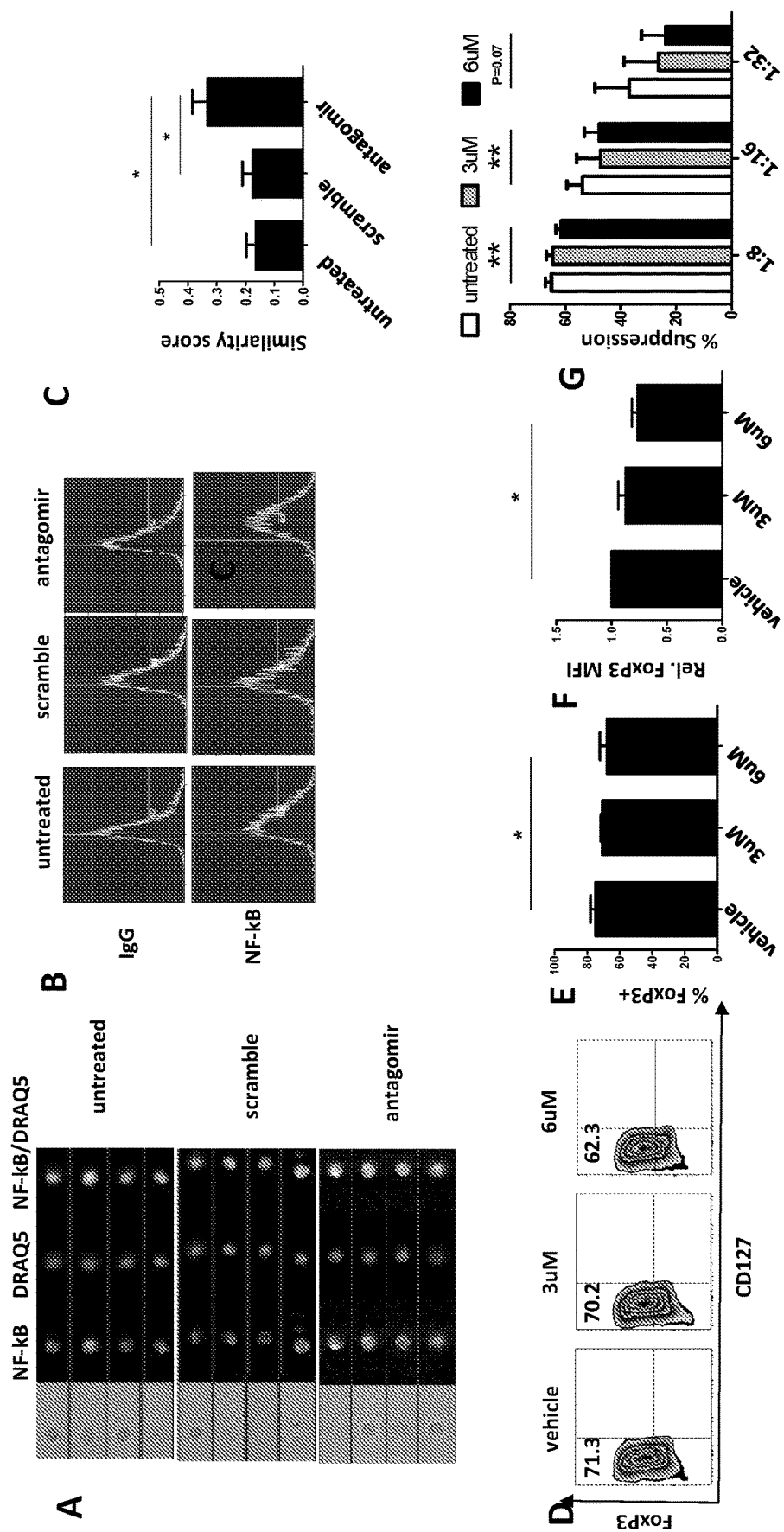
FIG. 12 is data showing that NF-kB activation is essential for human tTreg development and NF-kB is translocated into the nucleus after knock-down of miR-146b-5p. n=3 cells were left untreated, or were incubated with scramble RNA or miR-146b antagomir. Following treatment, cells were stained for CD4, NF-kB and DRAQS and NF-kB nuclear localization determined by imaging flow cytometry. Panel A are representative Imagestream images of cultured tTreg showing bright field images, as well as individual or overlaid images of NF-kB and DRAQS. Panel B is a representative and Panel C is a summary of similarity score measured by IDEA software quantitating the degree of overlap between NF-kB and DRAQS staining. Higher similarity scores indicate an increased nuclear localization. For Panels D through Panels G, naïve PB tTreg were purified, expanded in vitro and were either treated with DMSO only or with PS1145. Panel E is a graph showing a representative example of Foxp3 vs. CD127 staining on tTreg (gated on CD4+ cells). Panel F is a graph showing a summary of overall % Foxp3+CD127− cells. Panel G is a graph showing the level of Foxp3 expression, and CF SE assay for suppressive function in tTreg from each group. Values indicate mean±SEM of these experiments. (*P<0.05 and **P<0.01).

Example 20—Knock Down of miR-146b-5p Increases Nuclear Localization of NF-kB that is Key in Controlling tTreg Function TRAF6 is critical for TCR-mediated activation of NF-kB, and acts by ubiquitinylating TAK1, leading to activation of IKK and destruction of IkB, which allows NF-kB to translocate to the nucleus. To determine whether miR-146 antagomir enhanced NF-kB nuclear translocation, in vitro expanded tTreg were left untreated or treated for 2 days with scrambled RNA or miR-146b-5p antagomir, stained for CD4, NF-kB and DRAQS (a nuclear marker) and analyzed using imaging flow cytometry. Similarity feature was acquired to measure quantify translocation. By this method, a more composited/similar image by two colors means more translocation to nucleus. NF-kB in yellow and DRAQS in red are shown in FIG. 12A together with a composite image, more similar images were found in the antagomir group than in the untreated/scramble group. Following data acquisition, the spatial relationship between NF-kB and DRAQS was measured using the 'Similarity' feature in the IDEAS® software package (FIG. 12B). Similarity scores measure the pixel intensity correlation between the anti-NF-kB and DRAQS images, and increased similarity scores indicate increased overlap. As shown in FIG. 12C, antagomir treated tTreg cells demonstrated significantly higher similarity scores than untreated or scramble-treated tTregs, indicating increased NF-kB nuclear localization. These experiments demonstrated that NF-kB localization is regulated by miR-146b-5p.

NF-kB activation is critical for the development of tTreg in mice and positively regulates FoxP3 expression (Guckel et al., PLoS One, 2011, 6(5):e20003; Barbarulo et al., J. Immunol., 2011, 186(11):6199-206). To address the role of NF-kB in human tTreg, an inhibitor of NF-kB pathway (PS1145) was added for the final 2 days of culture (O'Shaughnessy et al., Am. J. Transplant, 2009, 9(3):452-62). NF-kB inhibition decreased Foxp3 expression in a dose-dependent manner, leading to significantly decreased in vitro suppressive function (FIG. 12D-12G). Therefore, NF-kB nuclear localization is associated with human tTreg function.

Figure 13:
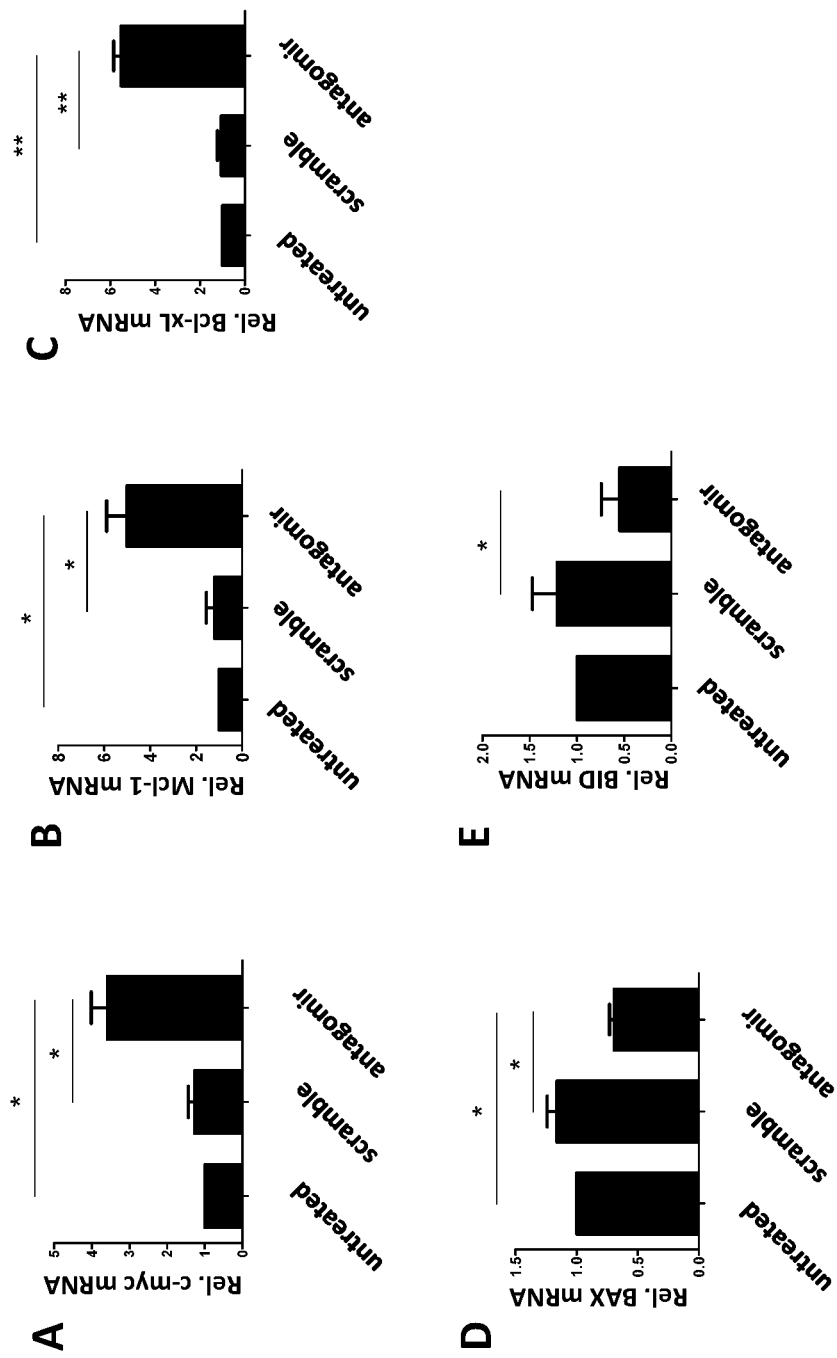
FIG. 13 are graphs showing that treatment with miR-146b-5p antagomir increases anti-apoptotic and decreases pro-apoptotic gene expression and enhances tTreg persistence and expansion. Naïve PB tTreg were sort purified, expanded in vitro and were either left untreated, or were incubated with scramble RNA or miR-146b antagomir. Following treatment, RNA was purified and qRT-PCR used to determine the expression of c-Myc (Panel A), anti-apoptotic genes Bcl-xL (Panel B) and Mcl-1 (Panel C), and pro-apoptotic genes BID (Panel D) and BAX (Panel E). Values indicate mean±SEM of these experiments. (*P<0.05 and **P<0.01).

Example 21—Antagomir-Treated tTreg Show Transcriptional Signs of NF-kB Activation NF-kB activation in T cells results in a series of transcriptional changes that up-regulates metabolism, cell cycle machinery and pro-survival pathways. To determine whether the basal increase in NF-kB nuclear localization observed in antagomir-treated tTreg had transcriptional consequences, the expression of known NF-kB-responsive genes was compared in antagomir-treated tTreg with those left untreated or treated with scramble RNA. One NF-kB target gene, c-myc, is a crucial regulator of T cell glycolysis, and promotes T cell-activation-induced growth and proliferation (Racker et al., PNAS USA, 1985, 82(11):3535-8; Wang et al., Immunity, 2011, 35(6):871-82). Thymocytes from miR-146b transgenic mice have defective IkB degradation following TCR stimulation, and attenuated induction of c-myc (Burger et al., Blood, 2014, 123(26):4089-100; Wei et al., Nat. Immunol., 2016, 17(3):277-85). As shown in FIG. 13A, antagomir treatment increased c-myc expression >3-fold over untreated or scramble-treated tTreg. In addition, consistent with the beneficial effects on viability and expansion, antagomir-treated tTreg had increased expression of anti-apoptotic members of the Bcl-2 family (Bcl-xL, Mcl-1) and decreased expression of pro-apoptotic members (BID, BAX) (FIG. 13B-13F).

Together, these data show that miR-146b-5p antagomir treatment of tTreg results in NF-kB activation and expression of pro-survival genes that increase tTreg in vitro expansion and suppressive function.

Figure 14:
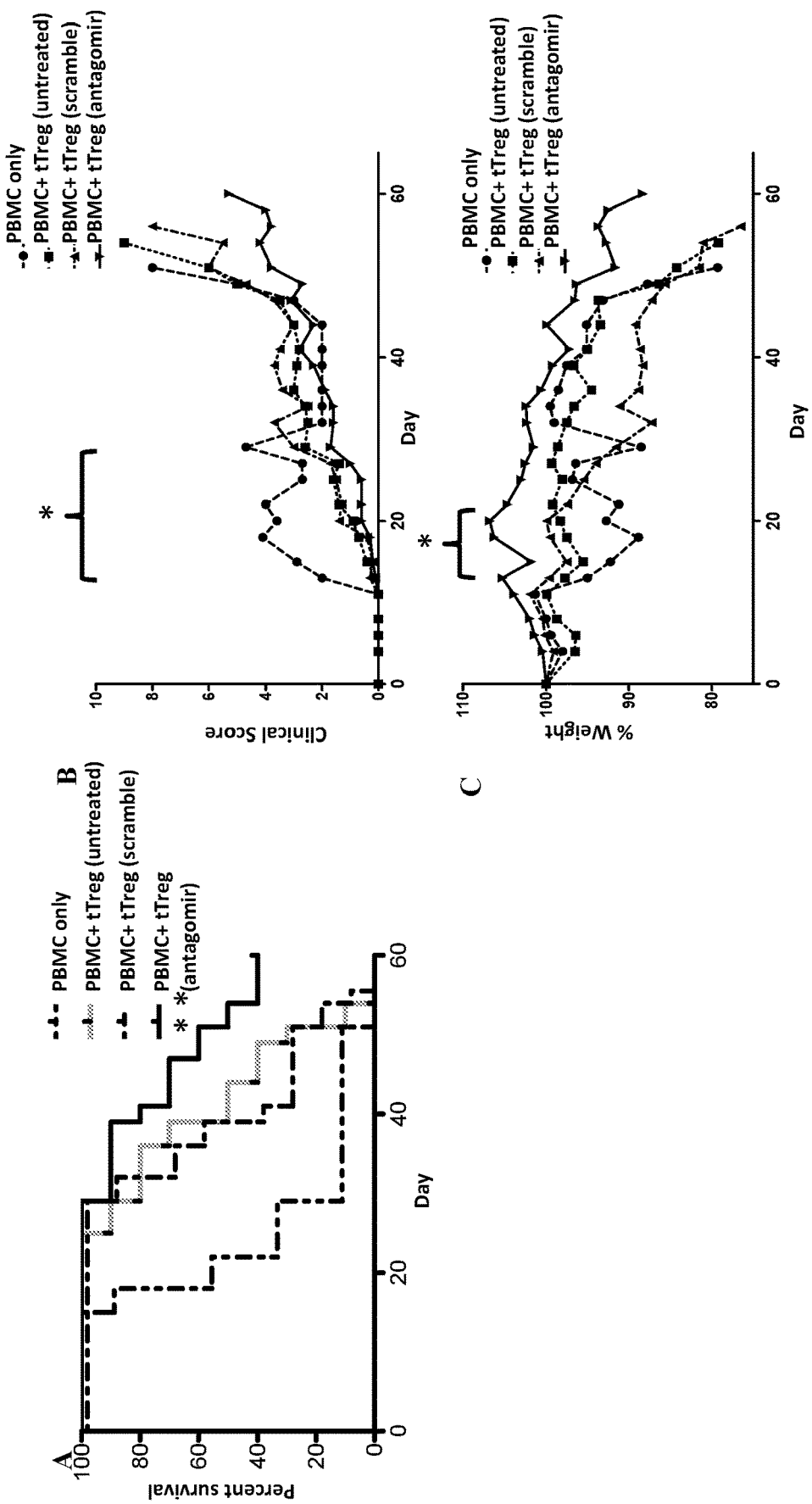
FIG. 14 is data showing that antagomir treated tTregs decrease mortality in a xenogeneic model of GVHD. Naïve PB tTreg were sort purified, expanded in vitro and were either left untreated, or were incubated with scramble RNA or miR-146b antagomir for two days. Following treatment, tTreg were washed and co-transferred (15×10$^6$) with allogeneic PBMC (15×10$^6$) into NOD/Scid/gamma c$^{-/-}$ mice to assess the ability to ameliorate xenogeneic GVHD. n=10, 10, 9 and 10 for groups PBMNCs, untreated, scramble and antagomir, respectively. Panel A shows the Kaplan-Meier survival curves for mice receiving PBMC±groups of tTreg (* P<0.05). Panel B shows the average weight (percentage of initial) for mice surviving on a given day for different groups of mice (*P<0.05 for all tTreg groups from days X to Y). Panel C shows the average GVHD score for mice surviving on a given day for different groups of mice (*P<0.05 for all tTreg groups from days X to Y). GVHD severity was measured by enumerating PBMC-derived (i.e., HLA-A2+) T cell numbers in circulation on day 14 in HLA-A2+ total (Panel D), CD4+ HLA-A2+(Panel E), and CD8+ HLA-A2+(Panel F) populations, respectively. Panel G shows in vivo tTreg persistence, which was determined by enumerating HLA-A2− cells in the blood on day 7. Panel H shows that the FoxP3+ tTreg population was maintained in all groups. Data shown are representative of 2 independent GVHD experiments.

Example 22—miR-146-5p Antagomir Treatment Significantly Increases Human tTreg Efficacy and Persistence in a Xenogeneic Model of GVHD Since miR-146b knock down enhances tTreg function, expansion and survival in vitro, we sought to determine whether miR-146b-5p antagomir-treated tTregs would be more effective at preventing xenogeneic GVHD. Ex vivo expanded tTregs (15×10$^6$) were untreated or treated with scramble or antagomir for 2 days, then injected with allogeneic PBMC (15×10$^6$) into NSG mice. As shown in FIG. 14A, all three groups of mice receiving tTreg had significantly reduced GVHD-induced lethality compared to PBMC-only controls (P<0.05, 0.01 and 0.001 for untreated, scramble and antagomir treated tTreg, respectively). Consistent with in vitro results, mice receiving antagomir-treated tTreg had significantly increased survival compared to mice receiving untreated or scramble-treated tTreg (P<0.05 and 0.05 for untreated and scramble-treated tTreg, respectively). Whereas no animals from the untreated tTreg control or scrambled groups survived past day 56, 40% receiving antagomir-treated tTreg survived beyond this day.

It was previously shown that adoptive transfer of tTreg ameliorates xGVHD-associated pathologies, weight loss, clinical scores and expansion of human T-cells in peripheral blood (PB). All cohorts of tTreg treated mice showed significantly decreased weight loss (P<0.05) between days 15 and 22, and decreased clinical scores between days 13 and 22 (FIGS. 14B and 14C, respectively). While mice receiving antagomir-treated tTreg lost less weight and developed fewer clinical symptoms than mice receiving untreated or scramble-treated tTreg, differences were not statistically significant.

Peripheral expansion of human T-cells on day 14-20 correlates inversely with survival. To quantitate the ability of each Treg cohort to minimize expansion, HLA-A2 mismatching was used to distinguish GVHD-causing PBMC (HLA-A2+) from tTreg (HLA-A2-). Mice were bled on day 14 and the total number of PBMC-derived cells/μl of blood enumerated (FIG. 14D). To assess T-cell expansion, the number of CD4+ HLA-A2+ and CD8+ HLA-A2+ cells/μl blood were quantitated (FIGS. 14E and 14F). All mice receiving tTreg had reduced PBMC-derived CD4 T-cell numbers, and mice receiving antagomir-treated tTreg had significantly fewer than mice receiving untreated or scramble-treated tTreg.

Previous studies found that tTreg persistence correlates with efficacy. We tested whether the enhanced survival of antagomir-treated tTreg seen in vitro might affect their persistence in vivo on day 7, 10 and 14. We have shown that, in both our xenogeneic GVHD model and in patients receiving third-party expanded tTreg, that tTreg are difficult to detect in PB beyond day 10-12. Not surprisingly, the cell number on day 10 was hard to detect and the number of tTreg observed on day 14 was not significantly higher than the PBMC only controls (which should have no HLA-A2+ cells) (data not shown). However, mice injected with miR-146b antagomir-treated tTregs had higher absolute numbers of circulating CD4+ HLA-A2− cells on day 7 (FIG. 14G) as compared to scrambled or untreated groups (7.8±3.2 cell/μl vs 4.6±3.2 cell/μl vs 4.4±3.5, P<0.05 for miR-146b antagomir versus either group). Importantly, as observed in vitro (FIG. 15B-15D), antagomir-treated tTreg maintained Foxp3 expression equivalently to untreated or scramble-treated tTreg (FIG. 14H). While increased PB tTreg numbers on day 7 is consistent with enhanced survival, other explanations include differences in expansion or homing.

Thus, knock down of miR-146b-5p in tTregs increases in vivo efficacy and can be exploited to improve the efficacy of adoptive Treg therapy for the prevention of human GVHD.

These results suggest a new target to increase tTreg efficiency based on miRNA level. These observations include: (1) both miR-146a and miR-146b-5p are highly differentially expressed in tTreg cells compared to control T-cells but these results suggested that, in contrast to miR-146a, miR-146-5p negatively regulates FoxP3 expression, expansion and tTreg function in vitro; (2) TRAF6, which plays an essential role in tTreg expansion and function, is a direct target of miRNA-146b-5p in human tTreg cells; (3) NF-kB pathway is vital for FoxP3 maintenance, miR-146b-5p antagomir treated tTreg cells show enhanced nuclear localization of NF-kB; (4) knock down of miRNA-146b-5p prolongs tTreg survival by regulating NF-kB-related apoptosis/anti-apoptosis genes; and (5) antagomir treatment enhances tTreg efficacy and persistence in a xenogeneic model of GVHD. In summary, knock down of miR-146b-5p in tTregs increases in vivo efficacy and can be exploited to improve the efficacy of adoptive Treg therapy for the prevention of human GVHD.

Example 23—Antagomirs Against Additional miRs

Figure 20:
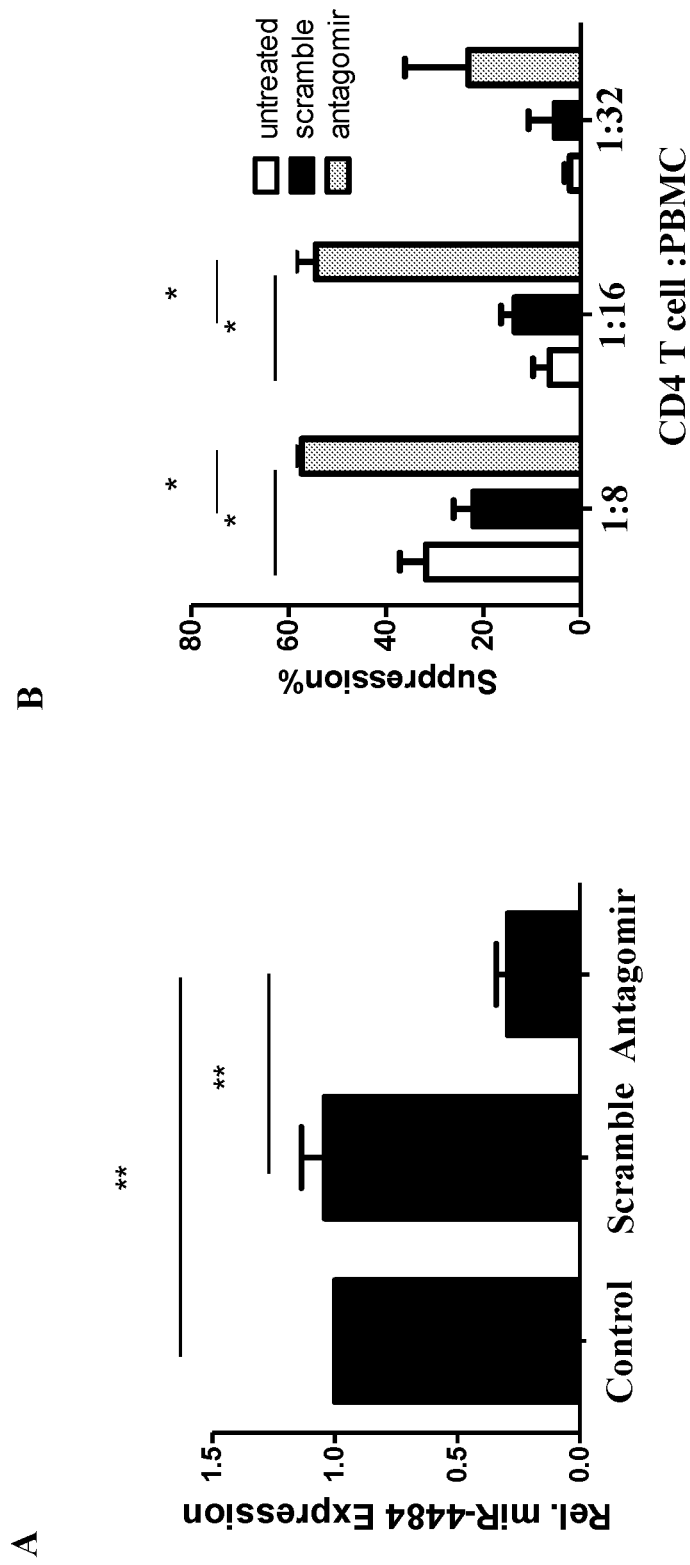
FIG. 20 is data showing that a miR-4484 antagomir induces suppressive function in expanded, naïve PB CD4+ (n=3 independent experiment). Panel A is a graph showing the efficiency of antagomir-mediated miR-4484 knock down. Panel B is a graph showing that treatment of CD4 Teff with miR-4484 antagomir induces suppressive function.

FIG. 20 shows that a miR-4484 antagomir induces suppressive function in expanded, naïve PB CD4+. Sorted, naïve CD4+/CD25− tTreg and CD4+ Teff cells were expanded with anti-CD3 mAb-loaded KT64/86 on days 0 and 7. Cells were exposed to a miR-4484 antagomir or a scrambled sequence on day 12, and harvested for flow cytometry on day 14. Panel A is a graph showing the efficiency of antagomir-mediated miR-4484 knock down in cells, and Panel B is a graph showing that treatment of CD4 Teff with miR-4484 antagomir induces suppressive function (n=3 independent experiments).

Figure 21:
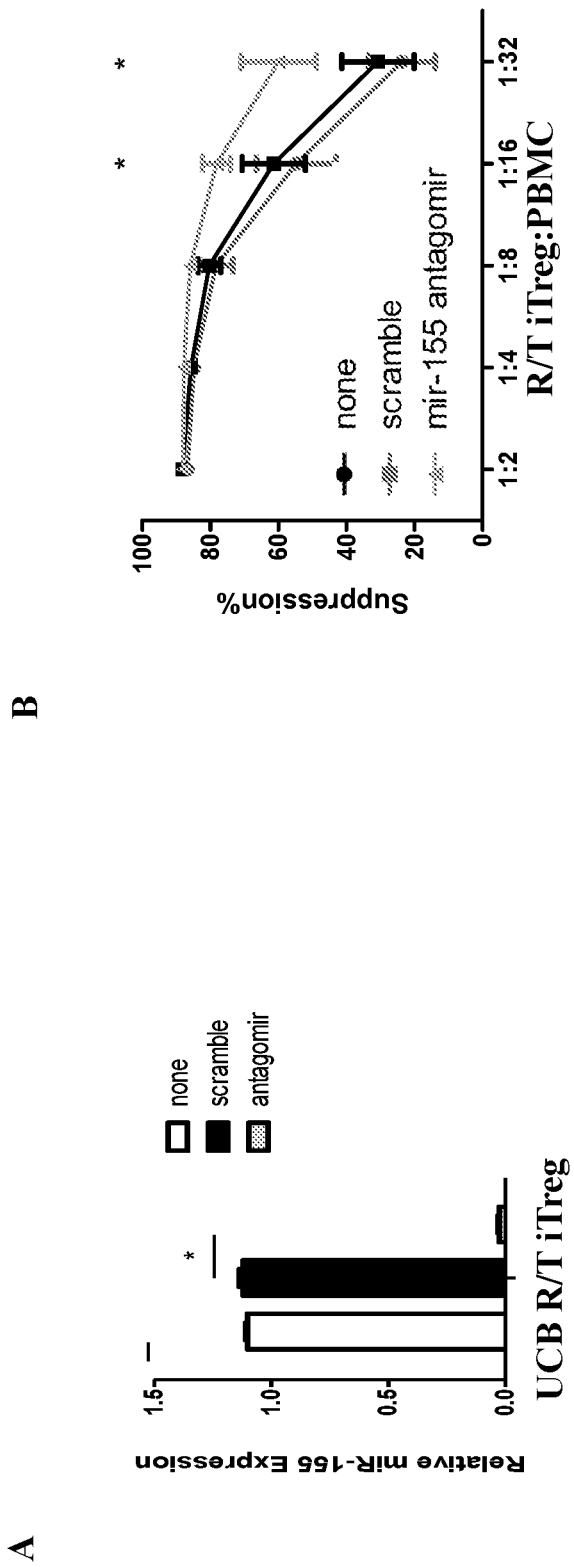
FIG. 21 is data showing that miR-155 antagomir increases suppressive function of UCB Rapa/TGF beta iTreg (n=3 independent experiments). Panel A is a graph showing the efficiency of antagomir-mediated miR-155 knock down. Panel B is a graph showing that treatment of UCB Rapa/TGF beta iTreg with miR-155 antagomir enhances suppressive function.

FIG. 21 shows that a miR-155 antagomir increases suppressive function of UCB Rapa/TGF beta iTreg. Sorted, naïve CD4+/CD25− tTreg and CD4+ Teff cells were expanded with anti-CD3 mAb-loaded KT64/86 on days 0 and 7, and cells were exposed to 50 mM of a miR-155 antagomir or a scrambled sequence on day 12. Cells were harvested for flow cytometry on day 14. Panel A is a graph showing the efficiency of antagomir-mediated miR-155 knock down, and Panel B is a graph showing that treatment of UCB Rapa/TGF beta iTreg with miR-155 antagomir enhances suppressive function (n=3 independent experiments).

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of increasing the survival, stability and/or function of Treg cells, comprising
providing Treg cells from an individual;
contacting the Treg cells with an miRNA-146b antagomir that inhibits miRNA-146b; and
introducing the contacted Treg cells back into the individual.

2. The method of claim 1, wherein the Treg cells are contacted with the moiety on day 0.

3. The method of claim 1, wherein the Treg cells are cultured for about 1 to about 21 days before being contacted with the moiety.

4. The method of claim 1, wherein the Treg cells are contacted with the moiety for several hours to several days to several weeks.

5. The method of claim 1, wherein the Treg cells are tTreg cells or iTreg cells.

* * * * *

SEQUENCE LISTING

<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
taacacgtct atacgccca                                                19

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
agcctatgga attcagttct c                                             21

<210> SEQ ID NO 3
<211> LENGTH: 60

```
<212> TYPE: RNA
<213> ORGANISM: Artificial Sequence
<220> FEATURE:
<223> OTHER INFORMATION: Synthetic oligonucleotide

<400> SEQUENCE: 3
ccuggaugau gauagcaaau gcugacugaa caugaagguc uuaauuagcu cuaacugacu      60

<210> SEQ ID NO 4
<211> LENGTH: 273
<212> TYPE: DNA
<213> ORGANISM: Homo sapiens

<400> SEQUENCE: 4
cttcagtctt tttgtagtat tatatgtaat atattaaaag tgaaaatcac taccgccttg      60
tgctagtgcc ctcgagaaga gttattgctc tagaaagttg agttctcatt tttttaacct     120
gttatagatt tcagaggatt tgaaccataa tccttggaaa acttaagttc tcattcaccc     180
cagtttttcc tccaggttgt tactaaggat attcagggat gagtttaaac cctaaatata     240
accttaatta tttagtgtaa acatgtctgt tga                                  273

<210> SEQ ID NO 5
<211> LENGTH: 273
<212> TYPE: DNA
<213> ORGANISM: Homo sapiens

<400> SEQUENCE: 5
cttcagtctt tttgtagtat tatatgtaat atattaaaag tgaaaatcac taccgccttg      60
tgctagtgcc ctcgagaaga gttattgctc tagaaagttg ctggagactt tttttaacct     120
gttatagatt tcagaggatt tgaaccataa tccttggaaa acttactgga gacttcaccc     180
cagtttttcc tccaggttgt tactaaggat attcagggat gagtttaaac cctaaatata     240
accttaatta tttagtgtaa acatgtctgt tga                                  273
```